United States Patent
Limem et al.

(10) Patent No.: US 10,532,127 B2
(45) Date of Patent: Jan. 14, 2020

(54) METHODS TO PRODUCE PERFORATED COLLAGEN COATED SURGICAL MESHES

(71) Applicant: Tepha, Inc., Lexington, MA (US)

(72) Inventors: Skander Limem, Melrose, MA (US); Bhavin Shah, Lowell, MA (US); Said Rizk, Windham, NH (US)

(73) Assignee: Tepha, Inc., Lexington, MA (US)

( * ) Notice: Subject to any disclaimer, the term of this patent is extended or adjusted under 35 U.S.C. 154(b) by 50 days.

(21) Appl. No.: 15/354,664

(22) Filed: Nov. 17, 2016

(65) Prior Publication Data
US 2017/0143872 A1    May 25, 2017

Related U.S. Application Data

(60) Provisional application No. 62/257,372, filed on Nov. 19, 2015.

(51) Int. Cl.
*A61L 27/34* (2006.01)
*A61F 2/00* (2006.01)
(Continued)

(52) U.S. Cl.
CPC ............ *A61L 27/34* (2013.01); *A61F 2/0036* (2013.01); *A61F 2/0059* (2013.01);
(Continued)

(58) Field of Classification Search
CPC .............. A61F 2240/001; A61F 2/0036; A61F 2/0059; A61F 2/0063; A61F 2/08
See application file for complete search history.

(56) References Cited

U.S. PATENT DOCUMENTS

| 3,276,448 A | 10/1966 | Kronenthal |
| 8,034,270 B2 | 10/2011 | Martin |
(Continued)

FOREIGN PATENT DOCUMENTS

| WO | 2006138098 | 12/2006 |
| WO | 2011119742 | 9/2011 |

OTHER PUBLICATIONS

Gorbet, et al., "Endotoxin: the uninvited guest," Biomaterials, 26:6811-7 (2005).
(Continued)

*Primary Examiner* — Christine H Matthews
(74) *Attorney, Agent, or Firm* — Pabst Patent Group LLP

(57) ABSTRACT

Methods to produce perforated collagen coated meshes for use as implants have been developed. The method involves positioning needles through the pores of the mesh, coating the mesh with a collagen solution, freezing the coated mesh, removing the needles from the frozen coated mesh, drying the collagen coated mesh, and optionally cross-linking the coated mesh. The method allows perforated collagen coated meshes to be prepared with variable thickness, and without damage to the surface of the mesh. The perforations of the collagen coated meshes may be designed to prevent the formation of fluid pockets when the coated meshes are implanted, and to permit rapid incorporation into host tissue. The perforated collagen coated meshes may be used for soft tissue repair, regeneration or remodeling including, for example, hernia repair, mastopexy, treatment of urinary incontinence, pelvic floor reconstruction, and ligament and tendon repair.

43 Claims, 12 Drawing Sheets

(51) Int. Cl.
*A61F 2/08* (2006.01)
*A61L 27/18* (2006.01)

(52) U.S. Cl.
CPC .............. *A61F 2/0063* (2013.01); *A61F 2/08* (2013.01); *A61L 27/18* (2013.01); *A61F 2240/001* (2013.01)

(56) References Cited

U.S. PATENT DOCUMENTS

| | | | |
|---|---|---|---|
| 2004/0197367 | A1 | 10/2004 | Rezania |
| 2012/0245705 | A1* | 9/2012 | Hasilo .................... A61F 2/022 623/23.72 |
| 2014/0044861 | A1* | 2/2014 | Boey .................... A61F 2/0063 427/2.24 |
| 2015/0148823 | A1* | 5/2015 | Mortarino ............. A61F 2/0063 606/151 |

OTHER PUBLICATIONS

Martin, et al., "Characterization of poly-4-hydroxybutyrate mesh for hernia repair applications," J. Surg. Res., 184:766-73 (2013).
International Search Report for corresponding PCT application PCT/US2016/062538 dated Mar. 8, 2017.

* cited by examiner

METHODS TO PRODUCE PERFORATED COLLAGEN COATED SURGICAL MESHES

CROSS-REFERENCE TO RELATED APPLICATIONS

This application claims the benefit of U.S. Provisional Application No. 62/257,372, filed on Nov. 19, 2015, the disclosure of which is incorporated herein by reference.

FIELD OF THE INVENTION

The present invention generally relates to the field of surgery, and more particularly, the invention relates to methods of forming perforated collagen coated mesh implants.

BACKGROUND OF THE INVENTION

Implantable meshes made from non-resorbable fibers, such as polypropylene and polyester, are well known in the prior art and are widely used in soft tissue repair. Implantable meshes made from resorbable fibers, or combinations of resorbable fibers and non-resorbable fibers, are also known in the prior art. For example, resorbable meshes, made from poly-4-hydroxybutyrate (P4HB), have been disclosed by Martin et al. *J. Surg. Res.* 184:766-773 (2013). Implantable meshes are used in procedures such as hernia repair, tendon and ligament repair, mastopexy, pelvic floor reconstruction, and treatment of urinary incontinence. The implantable meshes may be made from either monofilament fibers or multifilament fibers, or they may be made from both types of fibers. Multifilament meshes are generally softer and more compliant than monofilament meshes, however, surgeons often prefer to use monofilament meshes due to higher risks of bacterial contamination associated with the use of multifilament mesh.

Implantable meshes coated with collagen are also known in the art. Collagen coatings can be used to improve cell attachment to an implant, increase cell density on or in an implant, encourage tissue in-growth, increase revascularization, and improve incorporation of the implant in soft tissue. For example, collagen coatings can promote in-growth of fibroblasts and endothelial cells. Improved cell attachment and tissue in-growth can be particularly important in applications where it is desirable to reduce loss of strength during the early healing process. By encouraging earlier or more rapid tissue in-growth, collagen coatings can improve the short-term mechanical support provided by an implant. In addition to using collagen coatings as scaffolds to improve tissue in-growth, collagen coatings can also be used as matrices for delivery of bioactive agents. For example, collagen coatings on meshes can be used as matrices to deliver antimicrobial agents from implantable meshes.

One potential disadvantage of completely coating a mesh with a collagen coating is the possible formation of fluid pockets. These pockets can form, for example, at the site of soft tissue repair between the implant and the soft tissue, and interfere with tissue in-growth into the mesh and remodeling at the implant site.

WO 2011/119742 to Martin et al. discloses methods to completely encapsulate polyhydroxyalkanoate (PHA) mesh with collagen. The encapsulated mesh is prepared by immersing the PHA mesh in a collagen suspension, and drying. The process may be repeated to build up the thickness of the collagen coating on the mesh.

U.S. Pat. No. 3,276,448 to Kronenthal discloses methods of forming prostheses formed of porous, non-absorbable fabric coated with collagen. The methods, however, involve coating a porous fabric with collagen, and subsequently removing collagen from the pores of the fabric by directing a stream of an inert gas against the coated fabric, or alternatively, perforating the collagen coated fabric after the collagen has dried. In the former case, however, the method could result in too much collagen being stripped from the fabric or too little, and it is difficult to control the thickness of the collagen coating. In the latter case, perforating a collagen-coated fabric can result in damage to the underlying fabric resulting in decreased mechanical strength of the fabric.

It would therefore be desirable to identify a method to produce perforated collagen coated meshes that prevent the formation of fluid pockets and are more readily incorporated into host tissue. It would also be desirable to identify a method to produced perforated collagen coated meshes with defined coating thickness, and defined pore sizes and porosity.

It is therefore an object of the invention to provide a method to prepare a perforated collagen coated surgical mesh, without damaging the surface of the surgical mesh or its mechanical properties, and which affords control of the thickness of the collagen coating.

It is another object of the invention to provide an implant including a collagen-coated mesh with perforations that are formed through the pores of the mesh.

It is yet another objection of the invention to provide an implant for soft or hard tissue repair, wherein the implant comprises a collagen-coated mesh with perforations.

It is still a further object of the invention to provide methods to implant perforated collagen-coated meshes.

SUMMARY OF THE INVENTION

Methods to produce perforated collagen coated meshes for use as implants have been developed. The method involves positioning needles through the pores of the mesh, coating the mesh with a collagen solution, freezing the coated mesh, removing the needles from the frozen coated mesh, and drying the collagen coated mesh. If desired, the collagen may be cross-linked. The pore size of the perforations and the geometries of the perforations may be adjusted by using needles of different sizes and shapes, and the coated meshes may be prepared with different defined thicknesses and dimensions. The method allows perforated collagen coated meshes to be prepared with variable thickness, and without damage to the surface of the mesh. The perforations of the collagen coated meshes are designed to minimize the formation of fluid pockets when the coated meshes are implanted, and to permit rapid incorporation into host tissue.

Perforated collagen coated meshes prepared according to the methods disclosed herein are also disclosed. In one embodiment, the perforated collagen mesh includes perforations/channels which span the thickness of the collagen coated mesh.

The perforated collagen coated meshes may be used for soft or hard tissue repair, regeneration or remodeling including, for example, hernia repair, mastopexy, breast reconstruction, treatment of urinary incontinence, pelvic floor reconstruction, and ligament and tendon repair.

DETAILED DESCRIPTION OF THE INVENTION

Figure 1A:
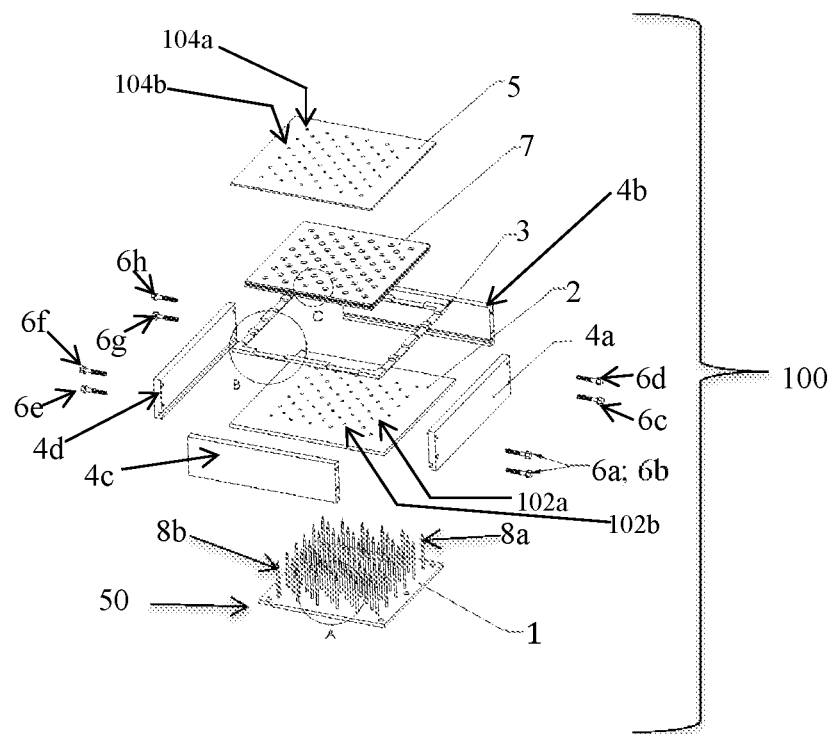
FIG. 1A is an exploded view a mold (100) used to manufacture a perforated collagen coated mesh (7). The mold includes the following parts: a needle plate (50) which includes a back plate (1) and needles 8a, 8b, etc., a base plate (2) with holes (102a; 102b; etc.) that match the pattern of the needles (8a; 8b; etc.) on the needle plate, a spacer rim plate (3), attachment frame plates (4a; 4b; 4c and 4d) that attach to the base plate using screws (6a; 6b; 6c; 6d; 6e; 6f; 6g and 6h), and a separation plate (5) with holes (104a; 104b; etc.) that match the pattern of the needles on the needle plate.

Methods are provided to manufacture perforated collagen coated meshes without damaging the surface of the mesh. The methods also allow perforated collagen coated meshes to be produced with a wide range of thicknesses that would be difficult to produce by standard coating techniques. The ability to produce these perforated collagen coated meshes has been made possible by the development of a new process wherein needles are inserted into the pores of the mesh prior to coating the mesh with collagen. During the process the needles prevent collagen from entering the pores, and the needles also make it possible to produce long perforations, of selected diameters, through thick collagen coatings that have been applied to the mesh. Importantly, the new method yields a perforated collagen coated mesh where the perforations have not become occluded with collagen, and the mesh surface has not been damaged.

The new method offers significant advantages over previously used methods. First, the method avoids causing surface damage to the mesh that can weaken the mesh. This could occur, for example, if the mesh was coated with collagen, and then perforated by drilling holes in the mesh by mechanical means or with a laser. Drilling holes through a coated mesh can result in surface damage to the mesh and may even break the mesh fiber in places. This is particularly undesirable because it will result in decreased burst strength of the mesh, and therefore result in unpredictable burst strength. Furthermore, laser drilling through a collagen coated mesh can result in browning of the collagen. Second, the new method can be used to produce perforated collagen coated meshes with controlled thickness, uniform perforations, controlled pore sizes and controlled pore size distributions and location. This is readily accomplished since needles placed through the pores of the mesh will keep channels open through any thickness of collagen applied to the mesh. In contrast, coating a mesh with collagen and using a stream of inert gas to remove collagen from the pores as disclosed, for example, by U.S. Pat. No. 3,276,448 to Kronenthal becomes increasingly difficult as the thickness of the coating is increased. Removing collagen from the perforations using a stream of inert gas also or creating pores in a collagen coated mesh using other methods such as freeze-drying, cannot produce uniform perforations through the collagen coated mesh. Unlike many alternative methods, the new method can also be used to produce perforated collagen meshes with larger pores, which can be sized by appropriate choice of needle diameters and mesh configuration.

In a preferred embodiment, the methods disclosed herein may be used to produce a perforated collagen coated mesh wherein just one side of the perforated mesh is coated with collagen. In this embodiment, a perforated collagen coating is only present on one side of the mesh. In a particularly preferred embodiment, the methods disclosed herein may be used to produce a perforated collagen coated mesh wherein both sides of the perforated mesh are coated with collagen. In this embodiment, the mesh is sandwiched between collagen layers.

The perforated collagen coated meshes may be used in soft or hard tissue repair, replacement or regeneration. In a preferred embodiment, the perforated collagen coated meshes are used for soft tissue repair, such as in hernia repair, breast reconstruction, mastopexy, plastic surgery, ligament and tendon repair, pelvic floor reconstruction and treatment of urinary incontinence. The collagen coating can be used to promote healing and repair by improving cell attachment to the implant and tissue in-growth, increase vascularization of the implant, and improve incorporation of the mesh into the local tissue. Perforations in the collagen coated mesh, produced using the new method, are particularly important to prevent the formation of fluid pockets after implantation between the tissue and the collagen coated mesh, and may lower seroma occurrence. Such pockets can prevent integration of the mesh into the tissue. The ability of the perforated collagen coated mesh to allow drainage of fluid is particularly important in breast reconstruction procedures where it is common for drains to be used post-surgery. To this end, the perforated collagen coated meshes offer improved drainage when compared to acellular dermal matrices or non-perforated collagen-based implants. In addition the perforations in the collagen coated mesh allow, if desired, easy placement of sutures through the mesh pores without damaging the mesh and decreasing its burst strength, and the perforations may also permit visualization of underlying tissue structures or devices. Furthermore, in procedures where implanted mesh may be palpable, for example, when it is implanted close to the surface of the body, such as under the skin, the collagen coating will decrease the ability of the patient to feel the implant. This is particularly important in certain plastic surgery procedures, including, for example, mastopexy and face lift, brow lift and neck lift procedures. Importantly, the perforated collagen coated meshes are pliable and easy to handle, and can retain water after soaking, and may have a skin-like feel during handling.

The perforated collagen coated meshes may also be loaded with bioactive agents. The new method allows thicker perforated collagen coated meshes to be produced that provide greater capacity (i.e. more collagen) for delivery of bioactive agents, including, for example, antibiotics.

Importantly, the advantages of the perforated collagen coated meshes described herein do not come at the expense of mechanical performance. The methods disclosed herein can be used to prepare perforated collagen coated meshes with comparable burst strengths, tensile strengths, and suture pullout strengths to the uncoated meshes that they were prepared from. In other words, the burst strengths, tensile strengths and suture pullout strengths of the meshes to be coated are not significantly changed or decreased when they are coated with collagen and perforated.

I. Definitions

"Absorbable" as generally used herein means the material is degraded in the body, and the degradation products are eliminated or excreted from the body. The terms "absorbable", "resorbable", "degradable", and "erodible", with or without the prefix "bio", can be used interchangeably herein, to describe materials broken down and gradually absorbed, excreted, or eliminated by the body, whether degradation is due mainly to hydrolysis or mediated by metabolic processes.

"Bioactive agent" is used herein to refer to therapeutic, prophylactic or diagnostic agents, preferably agents that promote healing, repair, and the regeneration of host tissue, and also therapeutic agents that prevent, inhibit or eliminate infectious agents. Bioactive agents include physiologically or pharmacologically active substances that act locally or systemically in the body. A biologically active agent is a substance used for, for example, the treatment, prevention, diagnosis, cure, or mitigation of one or more symptoms or characteristics of a disease or disorder. The bioactive agent may be a substance that affects the structure or function of the body, or a pro-drug which becomes biologically active or more active after it has been placed in a physiological environment. Bioactive agents include biologically, physiologically, or pharmacologically active substances that act locally or systemically in the human or animal body. Examples can include, but are not limited to, small-molecule drugs, peptides, proteins, sugars, polysaccharides, nucleotides, oligonucleotides, and nucleic acid molecules such as aptamers, siRNA, miRNA and combinations thereof.

"Biocompatible" as generally used herein means the biological response to the material or implant being appropriate for the implant's intended application in vivo. Any metabolites of these materials should also be biocompatible.

"Blend" as generally used herein means a physical combination of different polymers, as opposed to a copolymer formed of two or more different monomers.

"Burst strength" as used herein is determined by test method ASTM D6797-02 "Standard test method for bursting strength of fabrics constant rate of extension (CRE) ball burst test," using a MTS Insight 5 universal testing machine or similar device. The testing fixture uses a ⅜ inch diameter ball.

"Copolymers of poly-4-hydroxybutyrate" as generally used herein means any polymer containing 4-hydroxybutyrate with one or more different hydroxy acid units.

"Diameter" as generally defined herein is determined according to the US Pharmacopeia (USP) standard for diameter of surgical sutures (USP 861).

"Elongation to break" as used herein means the increase in length of a material that occurs when tension is applied to break the material. It is expressed as a percentage of the material's original length.

"Endotoxin units" as used herein are determined using the limulus amebocyte lysate (LAL) assay as further described by Gorbet et al. Biomaterials, 26:6811-6817 (2005).

"Molecular weight" as used herein, unless otherwise specified, refers to the weight average molecular weight (Mw), not the number average molecular weight (Mn), and is measured by GPC relative to polystyrene.

"Poly-4-hydroxybutyrate" as generally used herein means a homopolymer containing 4-hydroxybutyrate units. It can be referred to herein as P4HB or TephaFLEX® biomaterial (manufactured by Tepha, Inc., Lexington, Mass.).

"Suture pullout strength" as used herein means the peak load (kg) at which an implant fails to retain a suture. It is determined using a tensile testing machine by securing an implant in a horizontal holding plate, threading a suture in a loop through the implant at a distance of 1 cm from the edge of the implant, and securing the suture arms in a fiber grip positioned above the implant. Testing is performed at a crosshead rate of 100 mm/min, and the peak load (kg) is recorded. The suture is selected so that the implant will fail before the suture fails.

"Tissue" as used herein includes both soft and hard tissues.

II. Compositions

Methods have been developed to produce perforated collagen coated meshes that can be used in vivo for soft or hard tissue repair, regeneration, or remodeling. In a preferred embodiment, the mesh is made from a polymer, copolymer or blend of polymers or copolymers. The polymers and copolymers can be non-resorbable or resorbable. At least as a result of the method used to make the meshes, the perforated collagen coated meshes do not have a significant percentage of partially closed or occluded perforations.

"Perforation" as used herein in connection with the disclosed perforated collagen mesh is distinct from "pores" which may additionally be present in the disclosed perforated mesh. "Perforated" is used to refer to pores that span the thickness of the collagen coated mesh (FIGS. 9A to 9D), which are distinct from pores that may be present on the collagen-coated mesh, but do not span the thickness of the mesh and do not create open channels from one side of the implant to the other side of the implant (obtained is a collagen coat is merely applied onto a polymeric mesh for example. The perforated collagen meshes disclosed herein include pores that are perforations and pores that are not perforations.

In one embodiment, at least 70% of the perforations through the implant are not occluded by any mesh fiber or collagen, and more preferably greater than 75%, 80%, 85%, 90%, 95% or 100% of the perforations are not partially occluded by either collagen or mesh fiber.

A. Polymers

Examples of non-resorbable polymers and copolymers that can be used to produce the mesh include (i) polymers and copolymers of ethylene and propylene, including ultra-high molecular weight polyethylene, ultra-high molecular weight polypropylene, polyethylene, and polypropylene, (ii) nylon, (iii) polyesters such as poly(ethylene terephthalate), (iv) poly(tetrafluoroethylene), (v) polyurethanes, (vi) poly (ether-urethanes), (vii) poly(methylmethacrylate), (viii) polyether ether ketone, (ix) polyolefins, and (x) poly(ethylene oxide).

In a preferred embodiment, the mesh is made from a resorbable polymer, copolymer or blend thereof. The mesh may, for example, be prepared from one or more the following polymers or copolymers including, but not limited to, polymers of glycolic acid, lactic acid, D-lactic acid, L-lactic acid, 1,4-dioxanone, trimethylene carbonate, 3-hydroxybutyrate, 4-hydroxybutyrate, ε-caprolactone, including polyglycolic acid, polylactic acid, polydioxanone, polycaprolactone, copolymers of glycolic and lactic acids, such as VICRYL® polymer, MAXON® and MONOCRYL® polymers, and poly(lactide-co-caprolactones); poly(orthoesters); polyanhydrides; poly(phosphazenes); polyhydroxyalkanoates; synthetically or biologically prepared polyesters; polycarbonates; tyrosine polycarbonates; polyamides (including synthetic and natural polyamides, polypeptides, and poly(amino acids)); polyesteramides; poly(alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); silk (including recombinant silks and silk derivatives and analogs); chitin; chitosan; modified chitosan; biocompatible polysaccharides; hydrophilic or water soluble polymers, such as polyethylene glycol, (PEG) or polyvinyl pyrrolidone (PVP), with blocks of other biocompatible or biodegradable polymers, for example, poly(lactide), poly(lactide-co-glycolide), or polycaprolactone and copolymers thereof, including random copolymers and block copolymers thereof. Preferably the polymer, copolymer or blend thereof will be substantially resorbed within a 1 to 24 month timeframe, and retain some residual strength for at least 2 weeks-2 months, and more preferably at least 3-6 months.

In one preferred embodiment, polypropylene or non-resorbable polyester is used to make the mesh. In a particularly preferred embodiment, poly-4-hydroxybutyrate (P4HB) or a copolymer thereof is used to make the mesh. Copolymers include P4HB with another hydroxyacid, such as 3-hydroxybutyrate, and P4HB with glycolic acid or lactic acid monomer. Poly-4-hydroxybutyrate (P4HB, TephaFLEX® biomaterial) is a strong, pliable thermoplastic polyester that is biocompatible and resorbable (Williams, et al. Poly-4-hydroxybutyrate (P4HB): a new generation of resorbable medical devices for tissue repair and regeneration, *Biomed. Tech.* 58(5):439-452 (2013)). Upon implantation, P4HB hydrolyzes to its monomer, and the monomer is metabolized via the Krebs cycle to carbon dioxide and water. In a preferred embodiment, the P4HB homopolymer and copolymers thereof have a weight average molecular weight, Mw, within the range of 50 kDa to 1,200 kDa (by GPC relative to polystyrene) and more preferably from 100 kDa to 1000 kDa and even more preferably from 100 kDa to 600 kDa. A weight average molecular weight of the polymer of 50 kDa or higher is preferred for prolonged strength retention of the mesh.

B. Additives

Certain additives may be incorporated into the polymer, copolymer or blends thereof. Preferably, these additives are incorporated during a compounding process to produce pellets that can be subsequently melt-processed. For example, pellets may be extruded into fibers suitable for making the mesh. In another embodiment, these additives may be incorporated using a solution-based process, for example, fibers may be wet spun from solutions comprising one or more polymers or copolymers and one or more additives. In a preferred embodiment of the invention, the additives are biocompatible, and even more preferably the additives are both biocompatible and resorbable.

In one embodiment, the additives may be nucleating agents and/or plasticizers. These additives may be added in sufficient quantity to produce the desired result. In general, these additives may be added in amounts between 0.5% and 25% by weight. Nucleating agents may be incorporated to increase the rate of crystallization of the polymer, copolymer or blend. Such additives may be used, for example, to improve the mechanical properties of the fiber used to produce the mesh. Preferred nucleating agents include, but are not limited to, salts of organic acids such as calcium citrate, polymers or oligomers of PHA polymers and copolymers, high melting polymers such as PGA, talc, micronized mica, calcium carbonate, ammonium chloride, and aromatic amino acids such as tyrosine and phenylalanine.

Plasticizers that may be incorporated into the polymers, copolymers or blends thereof, include, but are not limited to, di-n-butyl maleate, methyl laureate, dibutyl fumarate, di(2- ethylhexyl) (dioctyl) maleate, paraffin, dodecanol, olive oil, soybean oil, polytetramethylene glycols, methyl oleate, n-propyl oleate, tetrahydofurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis(2-hydroxyethyl) dimerate, butyl ricinoleate, glyceryl tri-(acetyl ricinoleate), methyl ricinoleate, n-butyl acetyl rincinoleate, propylene glycol ricinoleate, diethyl succinate, diisobutyl adipate, dimethyl azelate, di(n-hexyl) azelate, tri-butyl phosphate, and mixtures thereof. Particularly preferred plasticizers are citrate esters.

In yet another embodiment of the invention, the additives are ceramics, more preferably bioceramics, and even more preferably resorbable bioceramics. Examples of resorbable bioceramics that can be incorporated into the polymers, copolymers or blends thereof include tricalcium phosphate (α and β forms of tricalcium phosphate (TCP)—with a nominal composition of $Ca_3(PO_4)_2$), biphasic calcium phosphate (BCP), hydroxylapatite, calcium sulfate, calcium carbonate, and other calcium phosphate salt-based bioceramics. Bio-active glasses may also be used. Bioactive glasses include bioactive glasses composed of $SiO_2$, $Na_2O$, CaO and $P_2O_5$ in specific proportions.

C. Collagen

The collagen used to coat the mesh may be derived from a natural source or it may be produced using a recombinant DNA technology. In one embodiment, the collagen may be derived from an equine, porcine, sheep, marine, or human source. In a preferred embodiment, the collagen is derived from a bovine source, and more preferably a bovine source certified to be free of bovine spongiform encephalopathy (BSE).

The collagen may be of the same fibrillar type, or a mixture of fibrillar types, including any of types I to XIII In a preferred embodiment, it may be a mixture of types I to III. In a particularly preferred embodiment, the collagen is predominantly type I, or solely type I.

The collagen used to coat the mesh is preferably in the form of a solution, slurry, or gel. The collagen may, for example, be in a neutral salt solution or dilute acid solution. In a preferred embodiment, the collagen is in a dilute acid solution. Examples of suitable solutions include collagen in acetic acid, citrate buffer or hydrochloric acid. Dilute solutions are generally preferred, such as acetic acid (0.5 M), or hydrochloric acid pH 2-3.5. A particularly preferred solution is 1% acid swollen bovine collagen gel produced by Devro Pty Ltd (Kelso, NSW, Australia). This solution has a pH of 2.9-3.1, fat content of ≤7%, ash content of ≤1%, and endotoxin content of ≤10 EU/mL.

The collagen may be processed by treatment with alkali or enzymes. These reagents may be used to cleave crosslinks and to suspend or dissolve acid-insoluble collagen structures. For example, the collagen may be processed using approximately 10% sodium hydroxide and 10% sodium sulfate. Or, the collagen may be treated with pepsin to provide collagen that can be swollen and solubilized. The collagen may also be subjected to treatments by denaturing agents and mechanical fragmentation, or subjected to chemical modification and derivatization, for example, by succinylation, acetylation, methylation or attachment of other polymers or chemical entities.

Other proteins may be added to the collagen solution, including both fibrous and globular proteins. In a preferred embodiment, gelatin can be added to the collagen solution.

D. Bioactive Agents

The perforated collagen coated meshes may comprise bioactive agents. These agents may be present in the mesh or collagen, or both the mesh and collagen, or may be present on the surface of the mesh or collagen, or both surfaces.

The bioactive agents may be used, for example, to improve wettability, water contact angle, cell attachment, tissue in-growth, or tissue maturation of the perforated collagen coated mesh. The bioactive agents may also be incorporated for the purposes of delivering bioactive agents in vivo. In a particularly preferred embodiment, the bioactive agents are delivered in the vicinity of the perforated collagen coated mesh.

In one embodiment, the perforated collagen coated meshes can contain cellular adhesion factors, including cell adhesion polypeptides. As used herein, the term "cell adhesion polypeptides" refers to compounds having at least two amino acids per molecule that are capable of binding cells via cell surface molecules. The cell adhesion polypeptides include any of the proteins of the extracellular matrix which are known to play a role in cell adhesion, including fibronectin, vitronectin, laminin, elastin, fibrinogen, collagen types II, and V, as well as synthetic peptides with similar cell adhesion properties. The cell adhesion polypeptides also include peptides derived from any of the aforementioned proteins, including fragments or sequences containing the binding domains.

In another embodiment, the perforated collagen coated meshes can incorporate wetting agents designed to improve the wettability of the surfaces of the mesh to improve collagen attachment to the mesh, or to allow fluids to be easily adsorbed onto the perforated collagen coated mesh surfaces in order to promote cell attachment, or modify the water contact angle of the perforated collagen coated mesh surface. Examples of wetting agents that can be incorporated into the perforated collagen coated meshes include polymers of ethylene oxide and propylene oxide, such as polyethylene oxide, polypropylene oxide, or copolymers of these, such as PLURONICS®. Other suitable wetting agents include surfactants or emulsifying agents.

In another embodiment, the perforated collagen coated meshes can contain bioactive agents designed to stimulate cell in-growth, including growth factors, hormones, cellular differentiating factors, cellular recruiting factors, cell receptors, cell-binding factors, cell signaling molecules, such as cytokines, and molecules to promote cell migration, cell division, cell proliferation and extracellular matrix deposition. Such bioactive agents include fibroblast growth factor (FGF), transforming growth factor (TGF), platelet derived growth factor (PDGF), epidermal growth factor (EGF), granulocyte-macrophage colony stimulation factor (GMCSF), vascular endothelial growth factor (VEGF), insulin-like growth factor (IGF), hepatocyte growth factor (HGF), interleukin-1-B (IL-1 B), interleukin-8 (IL-8), and nerve growth factor (NGF), and combinations thereof.

Other bioactive agents that can be incorporated include antimicrobial agents, in particular antibiotics, disinfectants, oncological agents, anti-scarring agents, anti-inflammatory agents, anesthetics, small molecule drugs, anti-angiogenic factors and pro-angiogenic factors, immunomodulatory agents, and blood clotting agents. Antimicrobial agents that may be incorporated into the perforated collagen coated meshes, include, but are not limited to, antibacterial drugs, antiviral agents, antifungal agents, and antiparisitic drugs. Antimicrobial agents include substances that kill or inhibit the growth of microbes such as microbicidal and microbiostatic agents. Antimicrobial agents that may be incorporated into the perforated collagen coated meshes, include, but are not limited to: rifampin; minocycline and its hydrochloride, sulfate, or phosphate salt; triclosan; chlorhexidine; vancomycin and its hydrochloride, sulfate, or phosphate salt; tetracycline and its hydrochloride, sulfate, or phosphate salt, and derivatives; gentamycin; cephalosporin antimicrobials; aztreonam; cefotetan and its disodium salt; loracarbef; cefoxitin and its sodium salt; cefazolin and its sodium salt; cefaclor; ceftibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt; cefadroxil; ceftazidime and its sodium salt; cephalexin; cefamandole nafate; cefepime and its hydrochloride, sulfate, and phosphate salt; cefdinir and its sodium salt; ceftriaxone and its sodium salt; cefixime and its sodium salt; cefpodoxime proxetil; meropenem and its sodium salt; imipenem and its sodium salt; cilastatin and its sodium salt; azithromycin; clarithromycin; dirithromycin; erythromycin and hydrochloride, sulfate, or phosphate salts, ethylsuccinate, and stearate forms thereof, clindamycin; clindamycin hydrochloride, sulfate, or phosphate salt; lincomycin and hydrochloride, sulfate, or phosphate salt thereof, tobramycin and its hydrochloride, sulfate, or phosphate salt; streptomycin and its hydrochloride, sulfate, or phosphate salt; neomycin and its hydrochloride, sulfate, or phosphate salt; acetyl sulfisoxazole; colistimethate and its sodium salt; quinupristin; dalfopristin; amoxicillin; ampicillin and its sodium salt; clavulanic acid and its sodium or potassium salt; penicillin G; penicillin G benzathine, or procaine salt; penicillin G sodium or potassium salt; carbenicillin and its disodium or indanyl disodium salt; piperacillin and its sodium salt; ticarcillin and its disodium salt; sulbactam and its sodium salt; moxifloxacin; ciprofloxacin; ofloxacin; levofloxacins; norfloxacin; gatifloxacin; trovafloxacin mesylate; alatrofloxacin mesylate; trimethoprim; sulfamethoxazole; demeclocycline and its hydrochloride, sulfate, or phosphate salt; doxycycline and its hydrochloride, sulfate, or phosphate salt; oxytetracycline and its hydrochloride, sulfate, or phosphate salt; chlortetracycline and its hydrochloride, sulfate, or phosphate salt; metronidazole; dapsone; atovaquone; rifabutin; linezolide; polymyxin B and its hydrochloride, sulfate, or phosphate salt; sulfacetamide and its sodium salt; clarithromycin; gentamicin; biguanide; bacitracin; silver, copper, zinc, and gold ions, salts, and complexes. In a preferred embodiment the antimicrobial agents incorporated into the implants are (i) rifampin and (ii) minocycline and its hydrochloride, sulfate, or phosphate salt. In a particularly preferred embodiment the perforated collagen coated meshes comprise rifampin and minocycline or its hydrochloride, sulfate, or phosphate salt.

The bioactive agents may be proteins such as antibodies, receptors, growth factors, hormones, and peptides, polysaccharides, including chitosan, alginate, and hyaluronic acid and derivatives thereof, nucleic acid molecules, including DNA, RNA, siRNA, miRNA, antisense or aptamers, small molecular weight compounds including steroids, inorganic materials such as hydroxyapatite, or complex mixtures such as platelet rich plasma.

Bioactive agents that can be incorporated into the perforated collagen coated meshes also include contrast agents, radiopaque markers, or radioactive substances.

In yet another preferred embodiment, the implants may incorporate systems for the controlled release of the therapeutic or prophylactic agents.

E. Cellular Components, Allograft, Autograft and Xenograft Materials

The perforated collagen coated mesh may further comprise cells, cellular components, allograft, autograft, and xenograft materials including microvascular tissues and cells. These components may also be seeded onto the perforated collagen coated mesh prior to implantation.

II. Methods of Preparing Perforated Collagen Coated Meshes

Figure 8A:
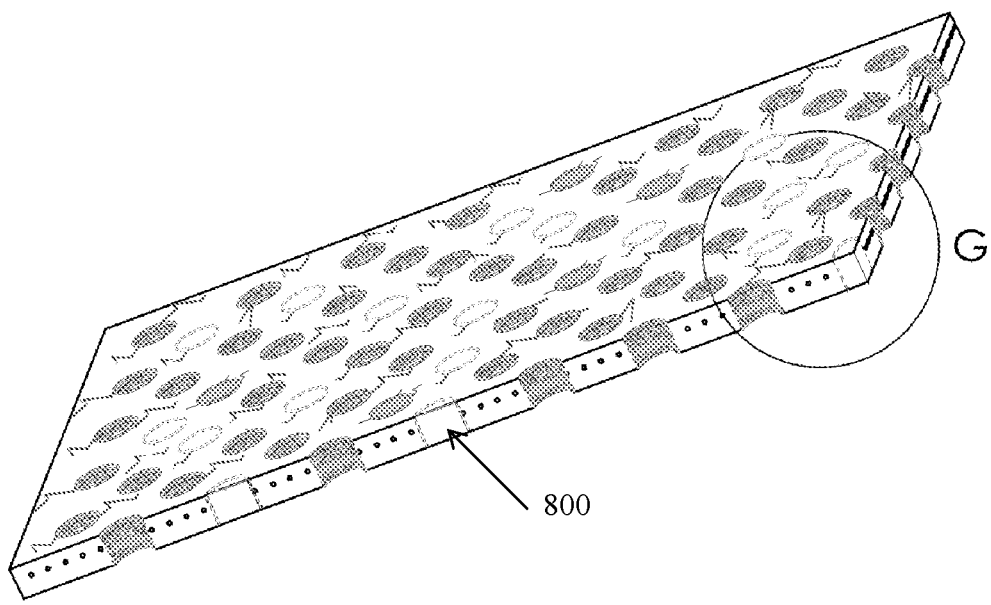
FIG. 8A shows a composite (800) of a P4HB mesh (804) encased with collagen which is prepared by encasing the mesh (804) with collagen, and freezing, then inserting the needles into the frozen composite with or without heating the needles.
Figure 8B:
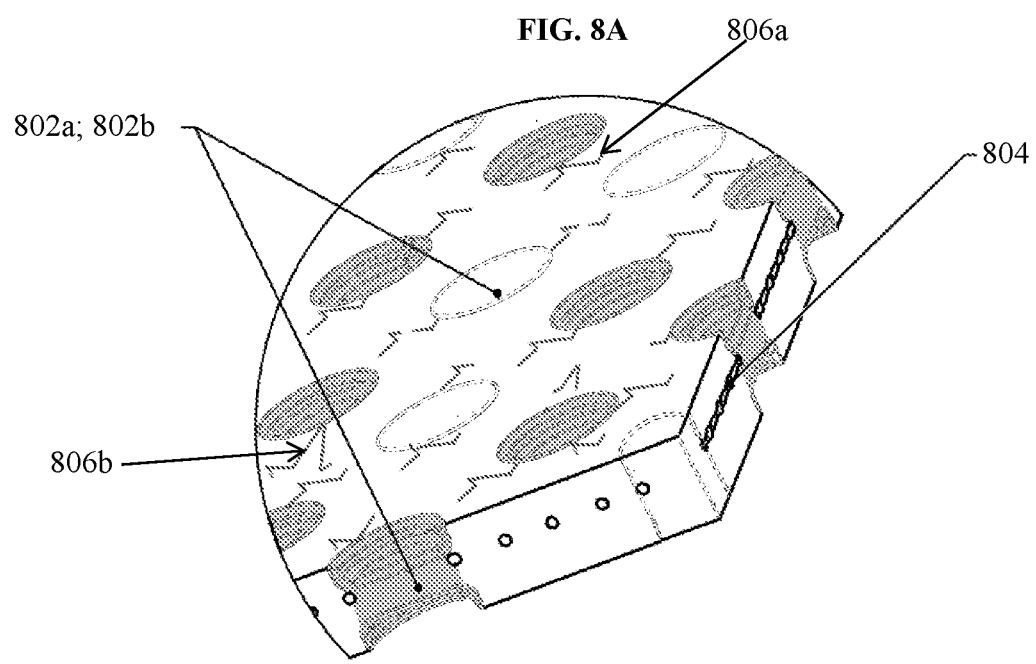
FIG. 8B is an enlarged view of a section (denoted G) of the composite (800) showing the damage that occurs to the composite when it is prepared by inserting needles into the pores of the mesh (804), encasing the mesh (804) with collagen, and freezing, but withdrawing the needles from the frozen composite without heating the needles.

Perforated collagen coated mesh implants have been developed wherein the perforations are completely aligned with pores in the mesh so as to provide straight open channels from one side of the implant to the other side of the implant. Accordingly, the length of the channel (created by the perforations) in these embodiments spans the thickness of the collagen coated mesh. Put another way, the fiber of the mesh or collagen material does not protrude into the perforations that run from one side of the implant to the other side. FIGS. 8A and 8B illustrate damage to a perforated collagen coated mesh that can occur as a result of the method by which the mesh is prepared, using methods that precoat a mesh with collagen and then create perforations, for example. When the needle bed is heated, the needles can be driven through a mesh precoated with collagen but this results in cracking of the construct. When the needle bed is cold, the needles can be driven through the construct by shear force and will result in the fracturing and partial melting of the construct. If a perforated composite is prepared by inserting needles into the pores of the mesh, encasing the mesh with collagen, and freezing, but withdrawing the needles from the frozen composite without heating the needles, the perforated composite is stuck to the needles and very hard to remove mechanically. Needles can only be removed when the collagen layers thaw, also resulting in occluded perforations. A construct showing the various types of damages is depicted in FIGS. 8A and 8B showing that the collagen flows back into the perforation (802a, 802b) formed and occludes it (represented by shading) and crack (806a, 806b; etc.).

By contrast, the methods disclosed herein by contrast provide implants that contain a very high percentage of completely open pore channels. In contrast to other methods used to coat meshes, the perforated collagen coated meshes do not have a significant percentage of partially closed or occluded perforations. In one embodiment, at least 70% of the perforations through the implant are not occluded by any mesh fiber or collagen, and more preferably greater than 75%, 80%, 85%, 90%, 95% or 100% of the pores are not partially occluded by either collagen or mesh fiber.

The methods disclosed herein also allow the mesh to be coated without causing any surface damage to the mesh, or breaking mesh fibers. Both surface damage and fiber breakage result in an undesirable loss of burst strength of the collagen coated mesh product.

A. Mesh Preparation

The mesh used to prepare the perforated collagen coated mesh may be produced by any suitable medical textiles technique. The mesh may be made from monofilament or multifilament fibers, preferably oriented fibers, and may be produced with fibers of resorbable or non-resorbable polymers, copolymers, or blends thereof. The mesh may be knitted, braided, woven or non-woven, but is preferably knitted. In an embodiment, the mesh has one or more of the following properties: an average thickness greater than 0.01 mm; an average thickness less than 25 mm; an average thickness between 0.01 mm and 25 mm; pore sizes greater than 0.01 mm in diameter; pores sizes less than 10 mm in diameter; pore sizes between 0.01 mm and less than 10 mm in diameter, including pore sizes greater than 0.1 mm in diameter and greater than 1 mm; a density of pores greater than 1 per square cm; a density of pores less than 50 per square cm; a density of pores between 1 and 50 per square cm, including greater than 5, 10, 15, 20, 25, 30, 35, 40, and 45 per square cm; burst strength greater than 1 kgf; burst strength less than 100 kgf; burst strength between 1 kgf and 100 kgf, including greater than 5, 10, 15, 20, 25, 30, 35, 40, 45, 50, 55, 60, 65, 70, 75, 80, 85, 90, 95 kfg. The mesh preferably has an areal density of 5 to 800 g/m$^2$.

In a preferred embodiment, the mesh is made from a polymer comprising one or more of the following monomers: glycolic acid, lactic acid, trimethylene carbonate, p-dioxanone, ε-caprolactone, 3-hydroxybutyrate, and 4-hydroxybutyrate. In a particularly preferred embodiment, the mesh is made from poly-4-hydroxybutyrate or copolymer thereof.

In a preferred embodiment, the mesh is made from monofilament fibers with average diameters between 0.001 mm and 1.0 mm. In another preferred embodiment, the monofilament fibers are USP sizes 5, 4, 3, 2, 1, 0, 2-0, 3-0, 4-0, 5-0, 6-0, 7-0, 8-0, 9-0, 10-0, 11-0, and 12-0 as defined by the United States Pharmacopeia (USP) for absorbable monofilament sutures, and are as shown in Table 1. For clarification, it is intended that both absorbable and non-absorbable monofilament fibers used to prepare the mesh may have the diameters shown in Table 1, or have average diameters between 0.001 mm and 1.0 mm. The monofilament fibers may be prepared by melt extrusion and solution spinning processes. Preferably, the monofilament fibers have a breaking strength between 0.01 kg and 100 kg, more preferably between 0.1 kg and 40 kg.

TABLE 1

Diameters Defined by the USP Standards for Absorbable Monofilament Sutures

| USP Suture Size | Average Min. Diameter (mm) | Average Max. Diameter (mm) |
|---|---|---|
| 12-0 | 0.001 | 0.009 |
| 11-0 | 0.010 | 0.019 |
| 10-0 | 0.020 | 0.029 |
| 9-0 | 0.030 | 0.039 |
| 8-0 | 0.040 | 0.049 |
| 7-0 | 0.050 | 0.069 |
| 6-0 | 0.070 | 0.099 |
| 5-0 | 0.10 | 0.149 |
| 4-0 | 0.15 | 0.199 |
| 3-0 | 0.20 | 0.249 |
| 2-0 | 0.30 | 0.339 |
| 0 | 0.35 | 0.399 |
| 1 | 0.40 | 0.499 |
| 2 | 0.50 | 0.599 |
| 3 and 4 | 0.60 | 0.699 |
| 5 | 0.70 | 0.799 |

In a preferred embodiment, the meshes are woven or knitted from monofilament fiber, and even more preferably from resorbable monofilament fiber. In a particularly preferred embodiment, the meshes are produced by either warp or weft knitting processes, however, a warp knit is preferred in order to minimize the stretching of the mesh structure. In a preferred embodiment, the mesh is made from polypropylene monofilament fibers or non-resorbable polyester multifilament fibers. In a particularly preferred embodiment, the mesh is made from poly-4-hydroxybutyrate (P4HB) monofilament fibers, P4HB multifilament fibers, or a combination of these fibers. Suitable methods for making the P4HB fibers by melt extrusion are described by WO 2011/119742 to Martin et al. and U.S. Pat. No. 8,034,270 to Martin et al. In a preferred embodiment, the P4HB fibers are oriented. In a particularly preferred embodiment, the P4HB fibers will have one or more of the following properties: a tensile strength of at least 100 MPa, more preferably at least 300 MPa, and even more preferably at least 500 MPa; an elongation to break of less than 500%, more preferably less than 300%, and even more preferably less than 100%, but greater than 5%; a tensile modulus of at least 100 MPa, more preferably at least 300 MPa, and even more preferably at least 500 MPa. In a particularly preferred embodiment, the P4HB monofilament fibers have tensile strengths higher than 600 MPa, preferably higher than 800 MPa, and more preferably higher than 900 MPa, 1,000 MPa, 1,100 MPa, 1,200 MPa, 1,300 MPa, or 1,400 MPa, but less than 1,500 MPa.

In an alternative embodiment, the mesh may be made from P4HB multifilament fibers. Methods to prepare P4HB multifilament fibers are described by WO 2011/119742 to Martin et al. and U.S. Pat. No. 8,034,270 to Martin et al. In an embodiment, the P4HB multifilament fibers are prepared with a denier per filament (dpf) of less than 10, preferably less than 6, more preferably less than 4, and even more preferably less than 3, but greater than 1. In a particularly preferred embodiment, the P4HB multifilament yarns have a denier per filament ranging from 1.7 to 9.0. In another embodiment, the multifilament fibers are prepared with a tenacity of greater than 2 gram/denier, more preferably greater than 4 gram/denier, and even more preferably greater than 9 or 9.5 grams per denier. In some embodiments, the P4HB multifilament yarns have a tenacity greater than 2 but less than 12. In another embodiment, the P4HB multifilament yarns have an average elongation to break of 10% to 70%, more preferably 10% to 40%.

A suitable knitted P4HB monofilament mesh may be prepared, for example, as follows: Monofilament P4HB fibers are mounted on a creel, aligned side by side and pulled under uniform tension to the upper surface of a "kiss" roller. The "kiss" roller is spun while semi-immersed in a bath filled with a 10% solution of Tween® 20 lubricant. The Tween® 20 lubricant is deposited on the surface of the sheet of fiber. Following the application of Tween® 20, the sheet of fiber is passed into a comb guide and then wound on a warp beam. A warp is a large wide cylinder onto which individual fibers are wound in parallel to provide a sheet of fibers. Next, warp beams are converted into a finished mesh fabric by means of interlocking knit loops. Eight warp beams are mounted in parallel onto tricot machine let-offs and fed into the knitting elements at a constant rate determined by the 'runner length'. Each individual monofilament fiber from each beam is fed through a series of dynamic tension elements down into the knitting 'guides'. Each fiber is passed through a single guide, which is fixed to a guide bar. The guide bar directs the fibers around the needles forming the mesh fabric structure. The mesh fabric is then pulled off the needles by the take down rollers at a constant rate of speed determined by the fabric 'quality'. The mesh fabric is then taken up and wound onto a roll ready for scouring. The P4HB monofilament mesh may be scoured ultrasonically with water, and heat set in hot water if desired. The mesh can be washed with a 70% aqueous ethanol solution.

B. Preparation of Perforated Collagen Coated Mesh

A method has been developed to allow perforated collagen coated mesh to be prepared that prevents collagen from partially or fully occluding the pores of the mesh. Needles are inserted into the pores of the mesh prior to coating the mesh, and remain in place during the collagen coating process in order to prevent the mesh pores from becoming partially or fully occluded. The needles make it possible to produce perforations through the collagen coated mesh that run from one side of the product, through a pore of the mesh, and exit on the other side of the product. The use of needles to create the perforations (prior to coating the mesh) is particularly advantageous because it allows the perforated collagen coated mesh to be prepared without any damage to the surface of the mesh or breakage of the fibers of the mesh. The needles also make it possible to produce perforated collagen coated meshes with long, or deep perforations that preferably span the thickness of the collagen coated mesh. Thus, it is possible to produce perforated collagen coated meshes with a range of thicknesses that would be difficult to achieve by building up layers of collagen using successive coatings. In this regard, the method makes it possible to produce perforated collagen coated meshes wherein the length of the perforations through the coated product range from an average thickness of 0.1 mm to an average thickness of 25 mm or more.

The use of needles to create perforated collagen coated meshes also makes it possible to accurately control the diameters of the perforations, which can range from 0.1 mm to 10 mm, as well as the density of the perforations in the product, which can range from 1 to 50 perforations per square cm. Different types of needles, needle patterns or configurations, and needle profiles, may be used to create different types of perforations in the collagen coated mesh. For example, the needles may be tapered in order to produce tapered perforations in the product. The needles may also have different cross-sectional shapes. For example, the needles may have round, elliptical, triangular, square, or diamond cross-sectional shapes in order to produce perforations with these shapes through the collagen coated product. The use of needles to manufacture the perforated collagen coated meshes also makes it possible to precisely control the pattern of the perforations in the collagen coated mesh. For example, perforated collagen coated meshes may be produced with random perforations, ordered or patterned perforations.

In an embodiment, the perforated collagen coated mesh is formed by positioning needles through the pores of the mesh to be coated, coating the mesh with a collagen solution, slurry or gel, freezing the collagen coated mesh with the needles left in place (through the mesh pores), and then removing the needles from the frozen coated mesh and drying the coated mesh.

Figure 1B:
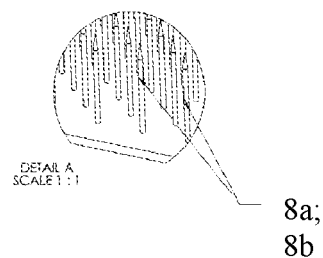
FIG. 1B is an enlarged view of a section (shown as Detail A) of the needle plate (50), that shows needles (8a; 8b, etc.) that are press fit to a back plate (1) to form the needle plate (50).
Figure 1C:
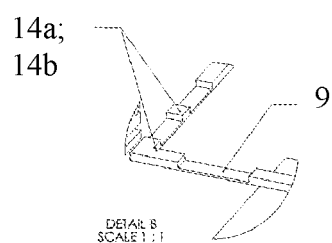
FIG. 1C is an enlarged view of a section (shown as Detail B) that shows a channel (9) and thickness control tabs (14a; 14b) on a section of the spacer rim plate (3).
Figure 1D:
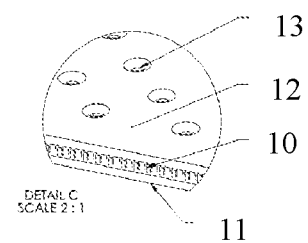
FIG. 1D is an enlarged view of a section (shown as Detail C) that shows a cross-section of the perforated collagen coated mesh (7) that can be formed with the mold where a mesh (10) is sandwiched between a bottom layer of collagen (11) and a top layer of collagen (12) with perforations (13) through the composite of collagen and mesh.
Figure 2A:
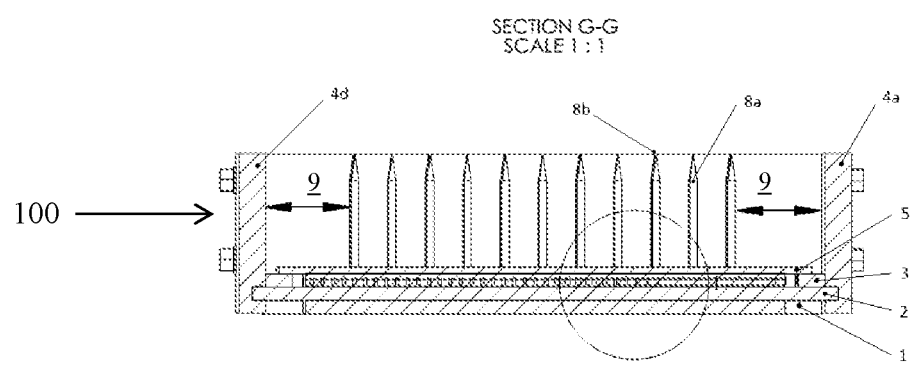
FIG. 2A shows a cross-section of an assembled mold (100) (FIG. 1A is an exploded view of the assembled mold (100) shown in FIG. 2A.
Figure 2B:
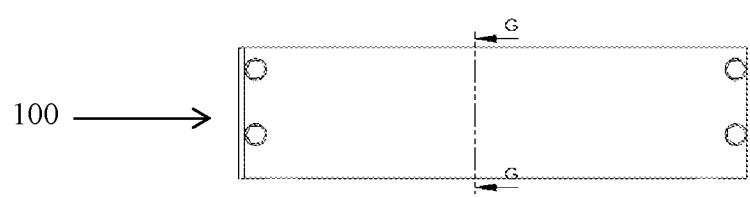
FIG. 2B is a cross section view of the mold shown in FIG. 2A (along the G-G line).
Figure 2C:
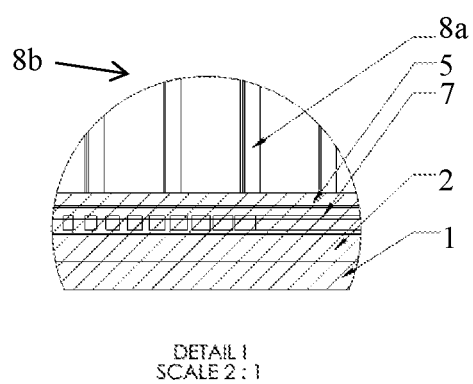
FIG. 2C is a diagram of an enlarged cross-section of the mold (100) used to manufacture a perforated collagen coated mesh showing the position of the needle plate (50), base plate (2), perforated collagen coated mesh (7) and needles (8a; 8b; etc.).
Figure 3:
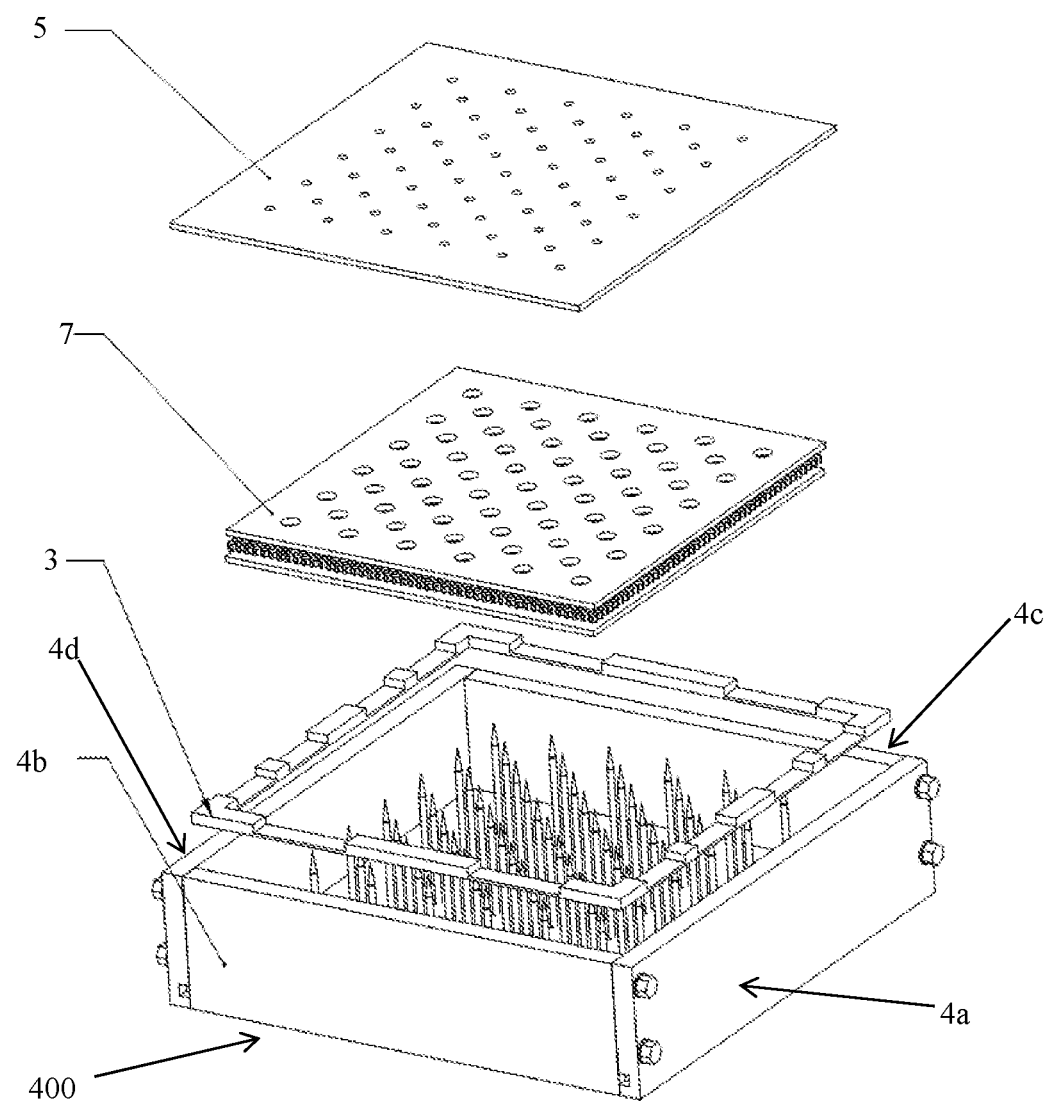
FIG. 3 is an exploded view of a partially assembled mold (400) used to manufacture a perforated collagen coated mesh showing the attachment of frame plates (4a; 4b; 4c; 4d) to the base plate, and the spacer rim plate (3) positioned ready for placement inside the frame plates. A collagen coated mesh (7) and separation plate (5) are also shown.

In a preferred embodiment, the perforated collagen coated mesh is formed using a mold assembly such as that shown in FIG. 1A. The assembly comprises: a needle plate (50) which includes a back plate (1) and a desired arrangement of needles (8a; 8b; etc.) fit onto a back plate, a base plate (2) with holes (102a; 102b; etc.) that match or are aligned with the needle pattern on the needle plate (50), frame plates (4) that attach to the base plate (2) to form a container for the collagen solution, slurry or gel (as shown in FIG. 3), a spacer rim plate (3) that controls the thickness of the perforated collagen coated mesh, and a perforated separation plate (5) with holes (6a; 6b; 6c; 6d; 6e; 6f; 6g and 6h) that are positioned to match the pattern of needles on the needle plate (50) and allow the needles to easily slide in and out of the holes. The back plate (1) optionally includes holes shown as (504a-505c in FIG. 5A) configured to receive mounting screws. The separation plate (5) is dimensioned to allow it to sit over the spacer rim plate (3) and create a uniform gap between its surface and the surface of the base plate (2). The needle plate (50) may be formed by press fitting needles, in the desired pattern, to a back plate (1) as shown in Detail A of FIG. 1B. The height of the frame plates when assembled, is matched to the needle height as shown in FIG. 2A. Preferably, the spacer rim plate (3) is formed with channels (9) as shown in FIG. 1C to allow excess collagen solution, slurry or gel to drain, with thickness control tabs (14a; 14b) on one or more sections of the spacer rim plate (3) as shown in Detail B in FIG. 1C. The thickness control tabs (14a; 14b) may be used to control the thickness of the collagen coated mesh. As shown in FIG. 2A, a gap (9) is provided between the perimeter of the needles of the needle plate (50) and the inside wall of the frame plates in order to accommodate the spacer rim plate inside the mold. FIG. 2A also shows how only the base plate (1) and ends of the frame plates (4a; 4b; 4c; 4d) are in contact with the working surface. FIG. 2C is a cross-section showing the location of the perforated collagen coated mesh (7) and the needles (8a; 8b). The perforated collagen coated mesh (7) is formed in the assembly between the base plate (2) and the perforated separation plate (5) as illustrated in FIG. 1A. The insert shown as Detail C in FIG. 1D shows a cross-section of the perforated collagen coated mesh that is formed in the assembly where the mesh (10) is sandwiched between a bottom layer of collagen (11) and a top layer of collagen (12) with perforations (13) through the collagen coated mesh composite.

In a preferred embodiment, the perforated collagen coated mesh is prepared with the assembly shown in FIG. 1A using the following procedure: (i) needles (8a; 8b; etc.) of the needle plate (50) are positioned through the pores of a mesh; (ii) the mesh is optionally heat set on the needle plate (50); (iii) the mesh is removed from the needle plate (50), and the needle plate (50) inserted into the base plate (2) until it is flush against one side of the base plate (2) with the needles protruding from the other side of the base plate (2); (iv) the frame plates (4a; 4b; 4c; and 4d) are attached to each side of the base plate (2) using the screws (6a-6h)) to form a container for the collagen solution, slurry, or gel; (v) the spacer rim plate (3) is inserted inside the container so that it is located on top of the base plate (2) and between the needles and inside wall of the frame plates (4a; 4b; 4c; 4d); (vi) a collagen solution, slurry or gel is poured to cover the base plate (2) to the desired depth; (vii) the mesh is replaced on the needles (8a; 8b; etc.) in the same orientation as previously used, and the mesh is then moved over the needles (8a; 8b; etc.) until it is in contact with the collagen solution; (viii) optionally (for a mesh encased in collagen) additional collagen solution, slurry or gel is then poured on top of the mesh to cover the mesh on both sides and completely encapsulate the mesh; (ix) the perforated separation plate (5) is aligned with the needles (8a; 8b; etc.) of the needle plate (50), and slid down the needles until it contacts the spacer rim plate (3) so that the mesh coated with collagen (7) is sandwiched between the perforated separation plate (5) and the base plate (2) with a thickness defined by the spacer rim plate (3); (x) the entire assembly containing the collagen coated mesh is frozen, and then the needles heated in order to release the needle plate (50) from the frozen collagen coated mesh; (xi) the needle plate (50) is removed from the assembly, and the remainder of the assembly disassembled to release the perforated frozen collagen coated mesh. The perforated collagen coated mesh is subsequently freeze-dried to form a perforated collagen coated mesh implant.

Figure 5A:
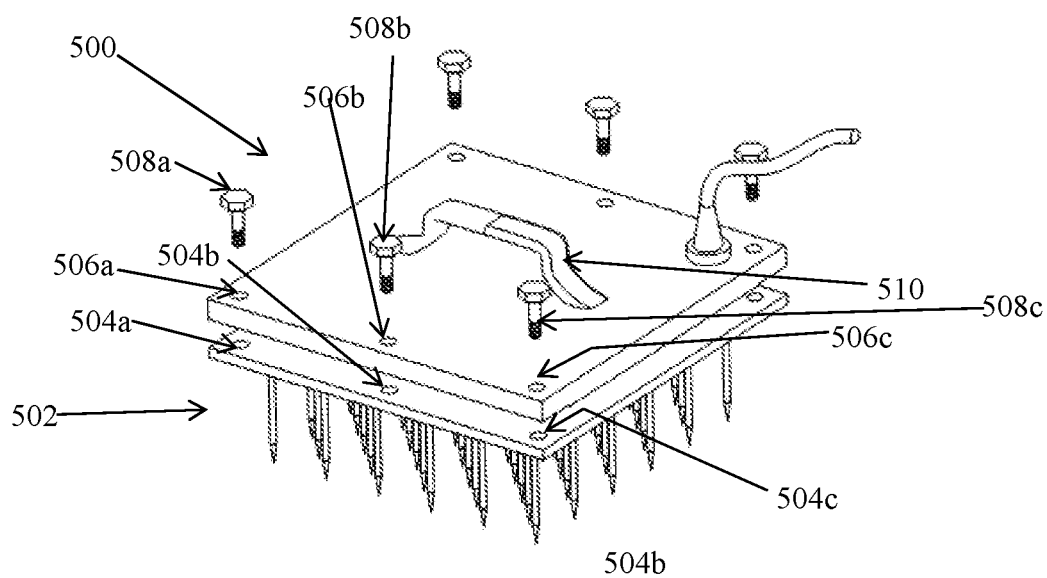
FIG. 5A is a diagram showing a heating plate (500) that can be attached to a needle plate (502), and a holding frame (51) (FIG. 5B) containing an assembled mold, shown in FIG. 3, used to prepare a perforated collagen coated mesh.
Figure 5B:
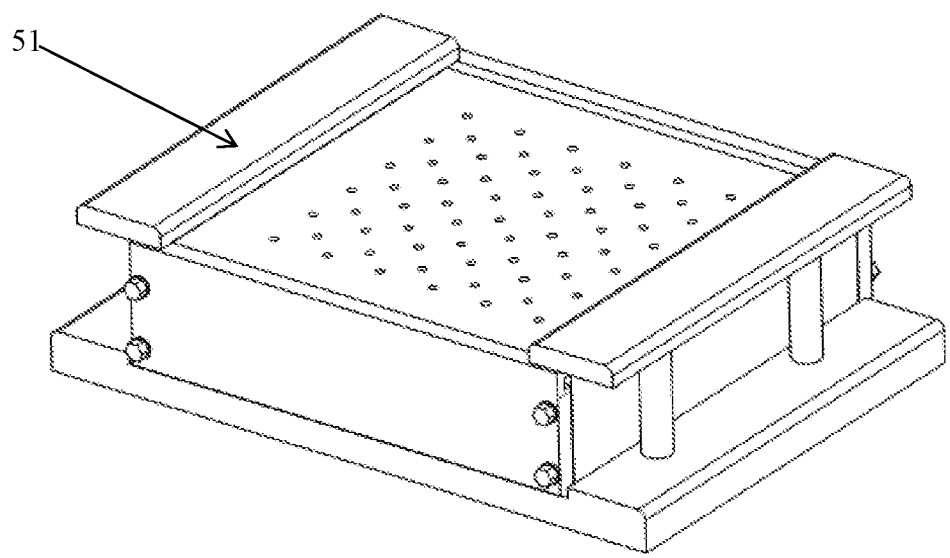

FIG. 5a shows a heating plate (500) and FIG. 5B shows a holding frame (51) that can be used to remove the needles of the needle plate from the frozen collagen coated mesh. The heating plate (500) can be attached to the needle plate (502) using mounting fixtures, and used to apply heat to the needles to allow local thawing of the frozen collagen in the immediate vicinity of the needles. Thawing of the collagen in the vicinity of the needles allows the needles to be withdrawn from the frozen collagen mesh composite without damaging the perforations formed by the needles. The heating plate (500) incorporates a heating element preferably with a power range of 5 to 50 watts. The heating plate is attached to a needle plate containing a perforated collagen mesh prepared as disclosed above using for example steps (i)-(x), but before removing the collagen mesh from the needle plate. In this embodiment, after freezing (in a freeze dryer for example), the frozen assembly is removed from the freeze dryer and inverted so that the bottom of the needle plate (502) is facing upward. The heating plate (500) is fastened to the needle bed and slid into the holding frame (51) (FIG. 5B). The heater is turned on to allow the needles to warm up and thaw the frozen composite in the vicinity of the needle stems.

In a particularly preferred embodiment, a perforated collagen coated monofilament knitted mesh made from poly-4-hydroxybutyrate fibers may be prepared using the assembly mold of FIG. 1 and the heating plate shown in FIG. 5 in the following manner. A poly-4-hydroxybutyrate (P4HB) monofilament knitted mesh, prepared as described above, is cut to the inside dimensions of the spacer rim plate (3) shown in FIG. 1A and carefully loaded onto tapered needles (8a; 8b; etc.) of the needle plate (50) using a medical grade brush so that the needles pass through pores of the monofilament knitted mesh. The mesh is then pushed down the needles until it lies on the bottom of the needle plate (50) i.e., on the back plate (1). This action forces the fibers of the P4HB mesh to adjust their positions around the perimeters of the needles, and sets up the perforation pattern that will be obtained in the collagen coated mesh.

Figure 6A:
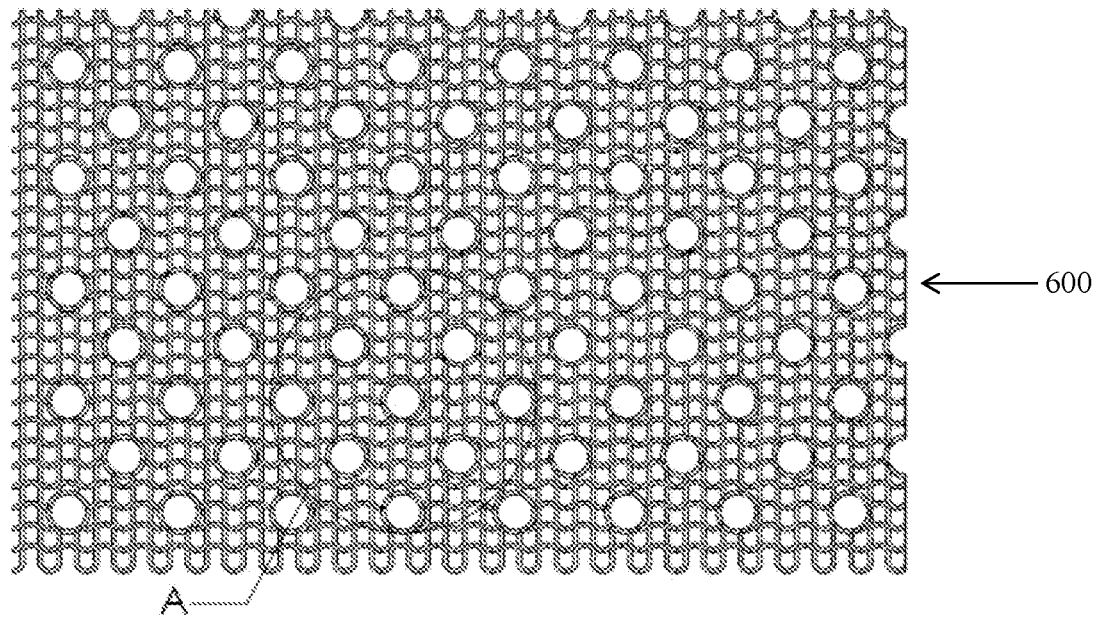
FIG. 6A shows a P4HB monofilament mesh (600) that has been perforated by placing the mesh on a needle plate and heat setting.
Figure 6B:
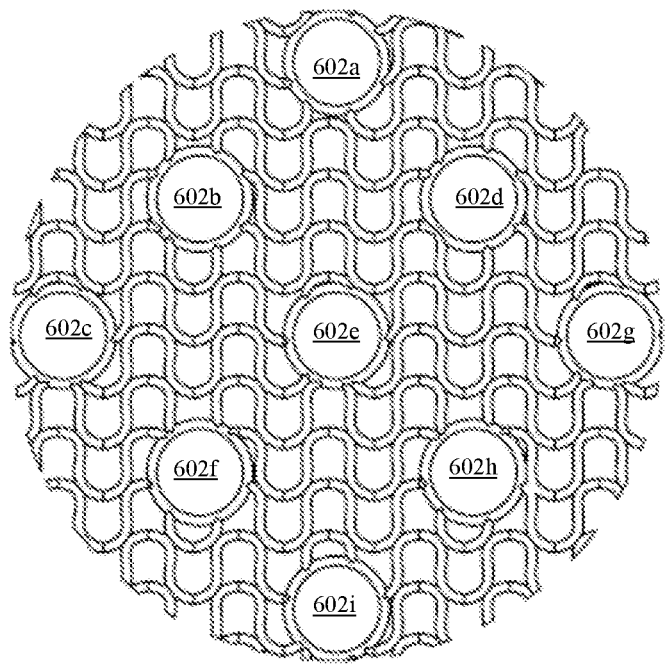
FIG. 6B is a magnified section of the mesh in FIG. 6A (identified as "A"), showing how needles and optionally heat setting create enlarged pores (602a; 602b; 602c; 602d; 602e; 602f; 602g; 602h and 602d) in the mesh (600).

Once the P4HB mesh has been loaded on the needle plate, the P4HB mesh is heat set. The P4HB mesh may be heat set by immersing the mesh loaded on the needle plate into a hot water bath set at 57° C. for 5 minutes. FIG. 6A shows a perforation pattern produced by a needle plate in a P4HB monofilament knitted mesh (600), after heat setting the mesh. As is evident from FIG. 6A, the needles caused some of the pores of the P4HB mesh to enlarge. A magnified image of the P4HB mesh is shown in FIG. 6B that demonstrates how the pores (602a-602i) of the mesh are enlarged by the needles, but without damage to the mesh fibers or overall structure of the P4HB mesh. After heat setting, the heat set P4HB mesh is allowed to cool, preferably to room temperature, and removed from the needle plate. In the next step of the process, frame plates (4) shown in FIG. 1A are attached to a base plate (2) using screws (6a-6f), and the needle plate (50) is inserted into and through the base plate (2) (as further illustrated by FIGS. 2 and 3). A spacer rim plate (3) shown in FIG. 1A is then placed inside the container formed by the frame plates (4a-4d) and on top of the base plate (2). An exploded view of the order of arrangement is shown in FIG. 3. FIG. 3 shows assembled frame plates (4a-4d) around a base plate (not visible) through which the needles (8A, 8b; etc.) of a needle plate are visible. A spacer rim plate (3) is shown in FIG. 3. An example of the cross-section of the complete assembly is shown in FIG. 2A. A collagen solution, slurry or gel is then poured over the bed of the needle plate, and optionally spread uniformly over the surface of the base plate (2) using a medical grade flexible brush. In a particularly preferred embodiment, a 1% acid swollen bovine collagen gel is used to coat the P4HB mesh. The P4HB mesh previously loaded on the needle plate is then re-loaded onto the needles in the same orientation, and gently pushed down the needles until it comes into full contact with the collagen solution, slurry or gel spread on the base plate. Optionally, for a P4HB mesh encased or sandwiched in collagen, additional collagen solution, slurry or gel is then poured and spread on top of the P4HB mesh until is it completely covered and to the desired depth. The separation plate (5) shown in FIG. 1 is then slid down the needles of the needle plate (50) until it makes contact with the spacer rim plate (3). The separation plate (5) is gently tapped to remove any excess collagen solution, slurry or gel via the flow channels of the separation plate. The mold assembly (FIG. 2A) containing the collagen coated P4HB mesh is then placed in a freeze dryer with the bottom of the needle plate (50) in contact with the freezing shelf of the freeze dryer, and the unit frozen to −40° C. at a freezing rate between 5 and 15° C. per hour.

After freezing, the frozen assembly is removed from the freeze dryer and inverted so that the bottom of the needle plate is facing upward. A heating plate (500) shown in FIG. 5A is fastened to the needle plate (502) using mounting screws, slid into the holding frame (51) (FIG. 5B), and the heater turned on for 3-5 minutes to allow the needles to warm up and thaw the frozen composite in the vicinity of the needle stems. The needle plate (502) is then removed from the collagen coated (frozen) mesh by lifting the heating plate that was fastened to the needle plate (502), and the remaining components of the mold containing the frozen collagen coated mesh removed from the holding frame. The mold is disassembled by removing: (i) the frame plates (4a-4d), (ii) the spacer rim plate (3), and (iii) the separation plate (5), and the frozen composite of the perforated collagen coated P4HB mesh is retrieved. While the collagen coated mesh is still frozen, it is placed on a stainless steel tray; a stainless steel mesh is placed over the frozen coated mesh to keep it flat, the tray put into a freeze-dryer, and the coated mesh dried over 15 hours. This process provides a dry perforated collagen coated P4HB mesh.

The perforated collagen coated mesh implants may contain graduation or orientation marks. These marks may assist the surgeon with the correct placement of the product in the surgical field, and with trimming the implant.

In another embodiment, a 3D shaped needle plate may be used to form a perforated 3D collagen coated mesh. In a particularly preferred embodiment a P4HB mesh is loaded on a 3D-shaped needle plate and heat set. This action forces the fibers of the P4HB mesh to adjust their positions around the perimeters of the needles and along the 3D profile of the needle plate. The P4HB mesh may be heat set by immersing the mesh loaded on the needle plate into a hot water bath set at 57° C. for 5 minutes. In this embodiment, the spacer rim plate and separation plate are also 3D shaped to match the same profile as the needle plate. The same manufacturing process described above is then followed to produce the 3D shaped perforated collagen coated mesh.

C. Cross-Linking of Perforated Collagen Coated Mesh

The perforated collagen coated meshes may be cross-linked. Crosslinking can be used to decrease the rate of resorption of the implant in the body. It can also be used to tailor the strength of the collagen coating of the implant. The perforated collagen coated meshes may be cross-linked by treatment with any of the following reagents: aldehydes, including formaldehyde and glutaraldehyde, hexamethylenediisocyanate, epoxy compounds, carbodiimides, including 1-ethyl-3-(3-dimethylaminopropyl)carbodiimide, and acyl azides. In a particularly preferred embodiment, the perforated collagen coated meshes are cross-linked with formaldehyde, and even more preferably the perforated collagen coated meshes are cross-linked with formaldehyde in the vapor phase. The perforated collagen coated meshes may also be cross-linked by physical means. For example, they may be cross-linked by heating, or by exposure to ultraviolet or gamma-irradiation.

Figure 7A:
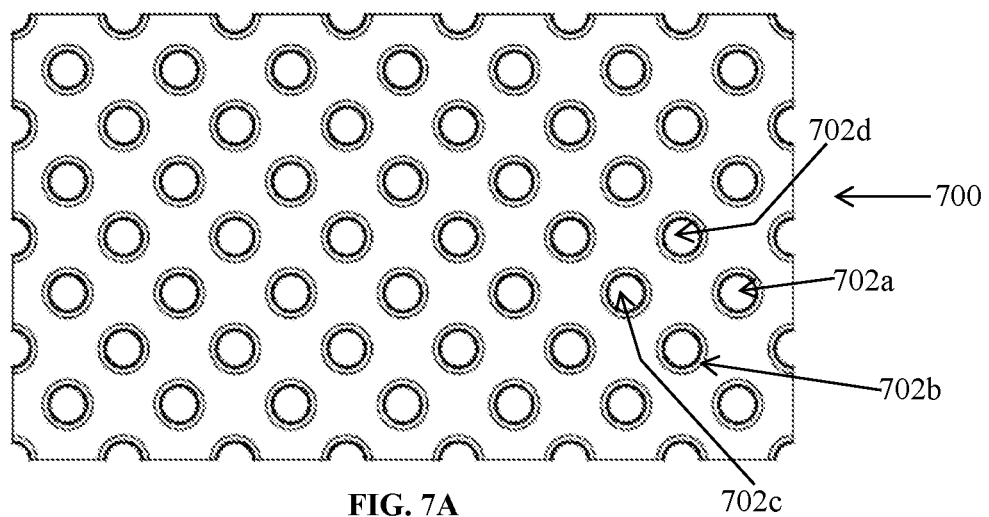
FIG. 7A shows the diamond perforated structure (700) of a P4HB monofilament mesh encased in cross-linked collagen.

In a particularly preferred embodiment, a dried perforated collagen coated mesh, prepared as described above, is cross-linked by placing the coated mesh in a vacuum chamber, exposing the coated mesh to formaldehyde vapor for one hour, and aerating the cross-linked perforated collagen coated mesh overnight. An example of a perforated cross-linked collagen coated mesh is shown in FIG. 7A.

In an embodiment, the degree of cross-linking of the perforated collagen coated mesh is between 10% and 60%, more preferably between 20% and 50%, and even more preferably between 30 and 40%. In another embodiment, the cross-linked perforated collagen coated mesh has a glass transition temperature between 50° C. and 90° C., more preferably between 60° C. and 80° C., and even more preferably between 60° C. and 70° C. as measured by Differential Scanning Calorimetry (DSC).

In a particularly preferred embodiment, perforated collagen coated P4HB, polypropylene, and non-resorbable polyester meshes are cross-linked.

D. Sterilization of Perforated Collagen Coated Mesh & Packaging

In an embodiment, the perforated collagen coated mesh is sterilized with dry heat, gamma-irradiation or by electron beam irradiation (e-beam). In a preferred embodiment the perforated collagen coated mesh is sterilized with ethylene oxide, and even more preferably with cold ethylene oxide. In an even more preferred embodiment, a perforated collagen coated P4HB monofilament knitted mesh is sterilized with cold ethylene oxide.

The perforated collagen coated meshes may be packaged in a protective envelope. In a preferred embodiment, the perforated collagen coated mesh is packaged in a protective envelope that is placed in a foil pouch with a Tyvek header to allow for ethylene oxide sterilization. In a particularly preferred embodiment, the protective envelope will be made from Tyvek. After exposure to ethylene oxide, the packaged collagen coated mesh is placed in a vacuum chamber and flushed with nitrogen to drive out any residual moisture and ethylene oxide. The foil pouch is sealed and the Tyvek header cut-off to maximize the product shelf life. Optionally, the sealed foil pouch is placed in an outer carton as part of secondary packaging for the perforated coated mesh.

III. Methods of Implanting

The perforated collagen coated meshes may be used in procedures for the repair, replacement or regeneration of hard or soft tissues. In a preferred embodiment the perforated collagen coated meshes are used in procedures for the repair, replacement, remodeling, lifting, or regeneration of soft tissues.

The perforated collagen coated meshes may be produced with permanent meshes, such as polypropylene mesh and non-resorbable polyester mesh, when long-term support is required. Alternatively the perforated collagen coated meshes may be produced with resorbable meshes, such as P4HB mesh, when temporary support is required. In one embodiment, the perforated collagen coated meshes are used in procedures where temporary support is required, for example, in certain repair, lifting, and remodeling procedures, including procedures where the tissue may be placed under tension, for example, breast lift, breast reconstruction, and pelvic floor reconstruction procedures. In a preferred embodiment, the perforated collagen coated meshes may be used in plastic surgery procedures, for example, to elevate, reinforce, replace or regenerate tissues in the face, neck, head, and breast. In a particularly preferred embodiment, the perforated collagen coated meshes are used in mastopexy procedures (breast lift procedures) and breast reconstruction procedures.

The perforated collagen coated meshes may also be used in conjunction with other implants. In a preferred embodiment the perforated collagen coated meshes may be used in conjunction with breast implants, for example, in breast reconstruction procedures, mastopexy procedures or other cosmetic procedures. The perforated collagen coated meshes may also be used to create pockets for implants, for example, in breast reconstruction procedures.

In another preferred embodiment, the perforated collagen coated meshes may be used for tissue support, either temporary or permanent, in hernia repair procedures, ligament and tendon repair, pelvic floor reconstruction and treatment of urinary incontinence.

In yet another embodiment, the perforated collagen coated meshes may be used in minimally invasive procedures. For example, the coated mesh implants may be used in a minimally invasive mastopexy procedure by implantation into a suitably dissected tissue plane to confer shape to the breast. The implants may, for example, be rolled up into a small cylindrical shape, placed inside a tubular inserter, and implanted through a small incision, such as a standard size incision at the inframammary fold that is usually used for breast augmentation. Once released in vivo, these coated mesh implants can be unrolled, and moved into position, for example, to confer shape to the host's breast tissue or an anatomical shape of the breast, and optionally fixated in position. In one preferred embodiment, the implant is delivered by employing an IMF incision used as the entry point for dissection, along with a periareolar incision, in a mastopexy procedure. Once skin removal and dissection is complete, the coated mesh implant can be deployed in vivo, unrolled, moved into place, and if desired, fixated. Alternatively, the three dimensional implants can be implanted using traditional open surgery techniques.

The perforated collagen coated mesh may, if desired, be fixated in vivo using standard fixation procedures, including suturing, gluing, stapling, and anchoring with devices such as tacks, hooks, and pins.

The present invention will be further understood by reference to the following non-limiting examples.

Example 1: Preparation of P4HB Monofilament by Melt Extrusion

Bulk poly-4-hydroxybutyrate (P4HB) resin in pellet form was dried to under 300 ppm water using a rotary vane vacuum pump system. The dried resin was transferred to an extruder feed hopper with nitrogen purge to keep the pellets dry. The pellets were gravity fed into a chilled feeder section and introduced into the extruder barrel, which was 1.50 inches in diameter and fitted with an extrusion screw with a 30:1 L/D ratio. The extruder barrel contained 5 heating zones (or extrusion zones)—zones 1, 2, 3, 4 and 5, and was manufactured by American Kuhne. The heated and softened resin from the extruder was fed into a heated metering pump (melt pump) and from the melt pump the extruded resin was fed into the heated block and an eight-hole spinneret assembly. Processing profile ranges from 40° C. to 260° C. for temperatures, and 400 psi to 2000 psi for pressures, were used. The molten filaments were water quenched and conveyed into a three-stage orientation, with inline relaxation, before winding of the monofilaments on spools. Test values for extruded monofilament fiber are shown in Table 1.

TABLE 1

Mechanical Test Data for P4HB Monofilament Fiber

| Fiber USP Size | Diameter, mm | Breaking Strength, Kg | Break Elongation |
| --- | --- | --- | --- |
| 5/0 | 0.150 | 1.80 | 30% |
| 6/0 | 0.100 | 1.00 | 29% |

Example 2: Preparation of a P4HB Monofilament Mesh

Spools with size 5/0 P4HB monofilament fiber prepared as described in Example 1 were converted into P4HB monofilament mesh as follows: Monofilament fibers from 49 spools were mounted on a creel, aligned side by side and pulled under uniform tension to the upper surface of a "kiss" roller. The "kiss" roller was spinning while semi-immersed in a bath filled with a 10% solution of Tween® 20 lubricant. The Tween® 20 lubricant was deposited on the surface of the sheet of fiber. Following the application of Tween® 20, the sheet of fiber was passed into a comb guide and then wound on a warp beam. A warp is a large wide cylinder onto which individual fibers are wound in parallel to provide a sheet of fibers. Next, warp beams were converted into a finished mesh fabric by means of interlocking knit loops. Eight warp beams were mounted in parallel onto tricot machine let-offs and fed into the knitting elements at a constant rate determined by the 'runner length'. Each individual monofilament fiber from each beam was fed through a series of dynamic tension elements down into the knitting 'guides'. Each fiber was passed through a single guide, which was fixed to a guide bar. The guide bar directed the fibers around the needles forming the mesh fabric structure. The mesh fabric was then pulled off the needles by the take down rollers at a constant rate of speed determined by the fabric 'quality'. The mesh fabric was then taken up and wound onto a roll ready for scouring. The P4HB monofilament mesh was scoured ultrasonically with water, and then washed with a 70% aqueous ethanol solution. The resulting mesh had two different pore sizes. A larger average pore size of 0.31 mm$^2$ (with an average diameter of 0.61 mm), and a smaller average pore size of 0.07 mm$^2$ (with an average diameter of 0.15 mm).

Example 3: Assembly for Making Perforated Collagen Coated Meshes

A mold as shown in FIG. 1A was prepared to manufacture the perforated collagen coated meshes. The mold consisted of five main components: a needle plate (50), base plate (2), spacer rim plate (3), frame plates (4a-4d) that attach to the base plate using screws (6a-6h), and a separation plate (5). FIG. 1A also shows a perforated collagen coated mesh (7) that is produced by the assembly.

The needle plate (50) consisted of stainless steel needles (8a; 8b; etc.) that were press fit onto a back plate (1) that was approx. 4 mm thick providing a flat stiff surface. The needles had a diameter of 1.4 mm, and a length of 20 mm. The height of the frame plates (4a-4d) was matched to the needle height (see cross-section of assembly in FIG. 2A), and the frame plates (4a-4d) were machined so that once attached to the base plate (2), the needle plate (50) could be inserted into the base plate (2) so that when assembled only the needle plate (50) and ends of the frame plates were in contact with the working surface (see FIG. 2A-2C). FIG. 2C also shows the location of the perforated collagen coated mesh (7) and the needles (8a; 8b, etc.).

FIG. 3 shows the mold after the needle plate has been inserted through the base plate (2), and the frame plates (4a-4d) attached to the base plate to form an assembled frame (400) which serves as a container for the collagen solution. FIG. 3 also shows the spacer rim plate (3) positioned over the assembled frame (400) and needles, and ready to be placed inside the assembled frame (400). The channels (9) in the spacer rim plate (shown in FIG. 1C) allow excess collagen solution to drain. Thickness control tabs (14a and 14b) (FIG. 1C) on the spacer rim plate (3) were used to control the thickness of the perforated coated mesh.

Figure 4A:
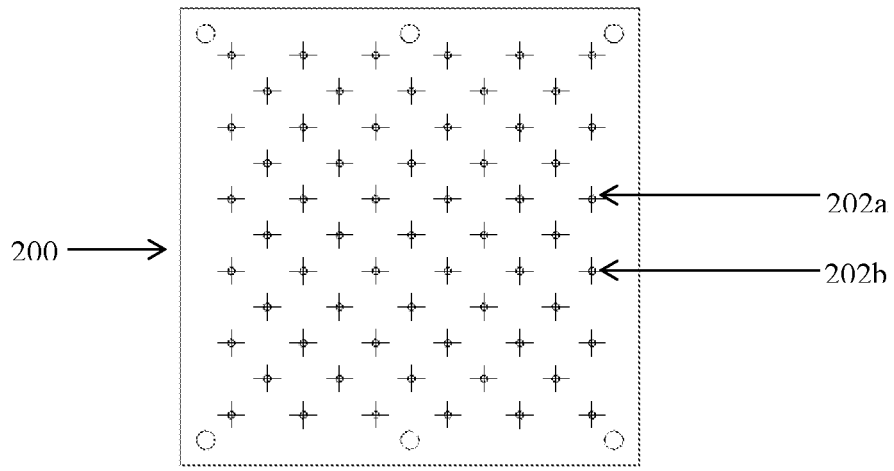
FIG. 4A is a diagram of a needle plate (200) showing a diamond pattern of needles (202a; 202b; etc.) used to form a diamond perforation pattern in a perforated collagen coated mesh.
Figure 4B:
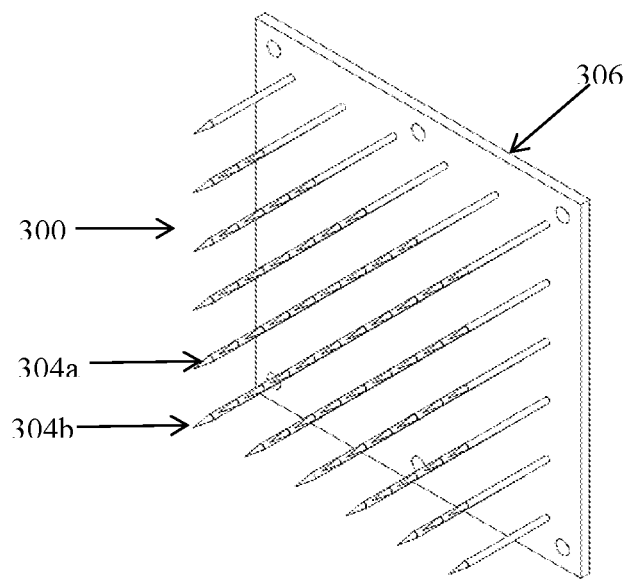
FIG. 4B is a diagram of a needle plate (300) showing circular tapered needles (304a, 304b; etc.) fixed in a diamond pattern to a back plate (306) to form a needle plate (300).

As shown in FIG. 2A, a gap (9) of at least 5 mm was left between the perimeter of the needles (8a; 8b; etc.) of the needle plate and the inside wall of the frame plates in order to provide room to insert the spacer rim plate inside the mold. The spacer rim plate was made from stainless steel, and was designed to run along the inside perimeter of the frame plates and sit flush against the base plate. The dimensions of the interior edge of the spacer rim plate determined the dimensions (length and width) of the perforated collagen coated mesh. The separation plate (5) shown in FIG. 1 was also made from stainless steel, with a thickness of about 2 mm, and consisted of a pattern of holes that matched the needle pattern on the needle plate (50) such that the needles on the needle plate could easily slide in and out of the holes on the separation plate. The outer dimensions of the separation plate (5) were set to allow the separation plate (5) to sit over the spacer rim plate (3) creating a uniform gap between its surface and the surface of the base plate. FIG. 4A shows the diamond pattern produced by the needles (304a; 304b; etc.) shown in FIG. 4B. The needles had round cross-sections and were tapered, and arranged with spacing between the needles of 6.4 mm to provide a density of 4 needles/cm$^2$.

In addition to the mold shown in FIG. 1A, a heating plate and holding frame were made in order to be able to heat the needles of the needle plate, and to retrieve the needle bed (after freezing of the mold assembly and perforated collagen coated mesh). The heating plate (500) and holding frame (51) are shown in FIGS. 5A and 5B. The heating plate included a metal base with fixture holes (represented on one side as 506a; 506b; 506c; that correspond in size and position to holes (504a; 504b; 504c) on the needle plate (502) and configured to receive screws (508a; 508; 508c; etc.) to mount the heating plate to the needle plate as shown in FIG. 5A, and a handle (510) to allow the easy removal of the heater from the mold assembly. The holes on the heating plate (500) and needle plate (502) are present on opposite sites as shown in FIG. 5A. The heating plate further included a flexible heating element (silicone heaters) with a power range of 5 to 50 watts.

Example 4: Preparation of a
Poly-4-hydroxybutyrate (P4HB) Perforated
Collagen Coated Mesh The mold shown in FIG. 1A was used to prepare a perforated P4HB collagen coated mesh as follows. A P4HB monofilament mesh prepared as described in Example 2, using the 0.15 mm diameter monofilament fiber prepared in Example 1, was cut to the size of the spacer rim plate (3). The mesh was tapped gently with a medical grade brush until it engaged the tapered end of the needles of the needle plate (50), and the needles (8a; 8b; etc.) passed through the mesh pores. The mesh was then driven down over the needles to the bottom of the needle plate (50). This action forced the knit fibers to adjust their positions around the perimeters of the needles, setting up the perforation pattern for the coated mesh. The needle plate loaded with the mesh was then immersed in a hot water bath set at 57° C. for 5 min in order to heat set the P4HB mesh to the needle pattern shown in FIG. 4A. The mesh loaded on the needle plate was then allowed to cool to room temperature, and the heat set mesh was removed from the needle plate. FIGS. 6A and 6B show the perforation pattern in the mesh after heating setting, and how the needles opened the mesh pores around the needles.

The frame plates (4a-4d) were then attached to the base plate (2) shown in FIG. 1A using the screws (6a-6h), and the needle plate (50) inserted into and through the base plate (2). The spacer rim plate (3) was then placed inside the mold on top of the base plate (2), and a solution of collagen (1% acid swollen bovine collagen gel, Collagen Solutions US Inc.) poured over the bed of the needle plate. The collagen solution was uniformly spread over the surface of the base plate (2) using a medical grade flexible brush. The heat set mesh was then loaded onto the needles in the same orientation used for heat setting, and the mesh gently tapped down the needles until it was in full contact with the collagen solution spread on the base plate surface. Additional collagen solution was poured over the mesh, and spread across the needles until all areas of the mesh were completely covered as shown in FIG. 1D where the mesh (10) is sandwiched between a bottom layer of collagen (11) and a top layer of collagen (12). The separation plate (5) was then slid down the needles of the needle plate (50) until it made contact with the spacer rim plate (3), and the separation plate gently tapped to remove any excess collagen solution via the flow channels (9) of the separation plate (FIG. 1C). The mold containing the collagen coated mesh was then placed in a freeze dryer with the bottom of the needle plate (50) in contact with the freezing shelf of the freeze dryer, and the unit frozen to −40° C. at a freezing rate between 5 and 15° C. per hour. After freezing, the frozen assembly was removed from the freeze dryer and inverted so that the bottom of the needle plate was facing upward.

Referring to FIGS. 5A and 5B, the heating plate (500) was fastened to the needle plate (502) using mounting screws (508a-508c shown for one side) on opposite sides of the heating plate, slid into the holding frame (51), and the heater turned on for 3-5 minutes to allow the needles to warm up and thaw the frozen composite (not shown in FIG. 5A) in the vicinity of the needle stems. The needle plate (502) was then removed by lifting the heating plate (500) that was fastened to the needle plate, and the mold containing the frozen collagen coated mesh removed from the holding frame (51). The mold was disassembled by removing the frame plates (4), the spacer rim plate (3), and the separation plate (5), and the frozen collagen with entrapped mesh retrieved. While the collagen coated mesh was still frozen, it was placed on a stainless steel tray; a stainless steel mesh was placed over the frozen coated mesh to keep it flat, the tray put into a freeze-dryer, and the coated mesh dried over 15 hours to yield a dry perforated collagen coated mesh.

Example 5: Cross-Linking of a Perforated Collagen
Coated P4HB Mesh

Figure 7B:
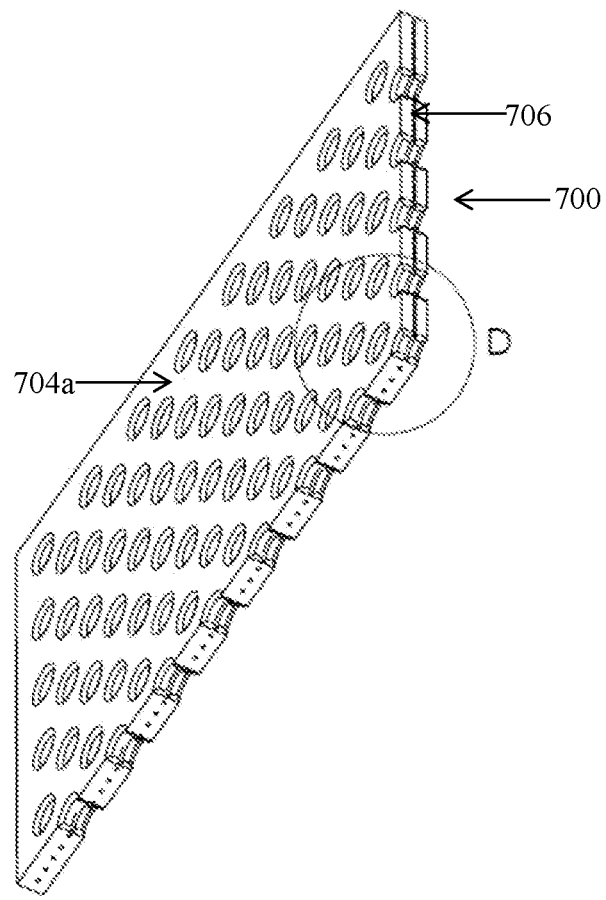
FIG. 7B is a dimetric view of the structure (700) shown in FIG. 7A, showing the uniform thickness of the composite.
Figure 7C:
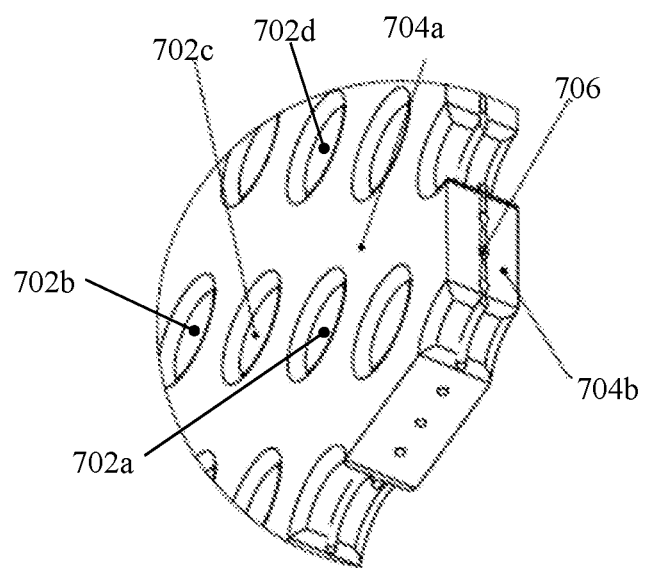
FIG. 7C is an enlarged view of a cross-section of the structure (700) designated as D in FIG. 7B, showing the perforations 702a; 702b; 702c; 702d etc., collagen layers (704a and 704b) and a mesh 706, embedded between the collagen layers.

The dried perforated collagen coated P4HB mesh prepared in example 4 was placed in a vacuum chamber, and exposed to formaldehyde vapor for 1 hour to cross-link the collagen. After exposure of the collagen coated mesh to formaldehyde, the perforated cross-linked collagen mesh was aerated overnight. FIG. 7A shows the perforated structure of the cross-linked collagen mesh, and FIG. 7B shows the uniform thickness of the cross-linked collagen mesh.

The average burst strength, average suture pullout strength, and average tensile strength of the uncoated P4HB mesh, uncoated perforated P4HB mesh (i.e. after loading onto the needles but before coating), and the cross-linked perforated collagen coated mesh were determined by testing 5 samples of each, and the results are shown in Table 2. As is evident from the results, the collagen coating perforation process did not negatively impact the mechanical properties of the underlying P4HB mesh. The burst strength, suture pullout strength and tensile strength values for the uncoated non-perforated P4HB mesh, uncoated perforated P4HB mesh and cross-linked perforated collagen coated P4HB mesh were very similar.

TABLE 2

Mechanical Test Data for Cross-linked Perforated Collagen Coated Poly-4-hydroxybutyrate (P4HB) Mesh.

| Specimen Tested | Burst Strength (Avg. in kgf) | Suture Pullout Strength (Avg. in kgf) | | Tensile Strength (Avg. in kgf) | |
| --- | --- | --- | --- | --- | --- |
| | | Machine Direction | Cross Machine Direction | Machine Direction | Cross Machine Direction |
| Cross-linked perforated collagen coated P4HB mesh | 21.8 | 5.4 | 4.1 | 5.0 | 5.6 |
| Uncoated perforated P4HB mesh | 20.2 | 4.6 | 5.0 | 6.0 | 3.5 |
| Uncoated non-perforated P4HB mesh | 20.8 | 5.0 | 4.5 | 5.2 | 5.3 |

Comparative Example 1: Attempted Preparation of
a P4HB Perforated Collagen Coated Mesh without
Heating the Needles Prior to Removal of the
Needle Plate Example 4 was repeated except the needles of the needle plate (50) were not heated prior to removal of the needles from the frozen collagen coated mesh. FIG. 8 shows the damage to the collagen coated mesh that occurs when the needles are withdrawn from the perforated collagen coated mesh without heating the needles. It was only possible to remove the composite from the needles and base plate after the composite had softened, and this resulted in breakage of the collagen coated mesh. The example demonstrates the need to heat the needles (or release the needles from the collagen) prior to removal of the composite from the needles.

Comparative Example 2: Attempted Preparation of a P4HB Perforated Collagen Coated Mesh by Driving Heated Needles Through a Frozen Collagen Coated P4HB Mesh Example 4 was repeated except a frozen collagen coated mesh was prepared without first placing needles through the pores and freezing, and the needle plate was used to pierce the frozen composite. A heat set mesh was placed on top of a collagen layer, and the mesh covered with collagen to form a non-perforated collagen coated mesh. The composite was frozen, and placed on a silicone pad located on a hard surface. The needle plate was warmed, and placed on the composite so that the needle tips were in contact with the frozen composite. This assembly was then placed between the jaws of a pressure clamp, and pressure was applied to force the needles through the frozen composite in order to create perforations. The frozen composite melted locally around the tips of the needles, and the needles pierced through the mesh. However, the thawed collagen solution flowed back into the pores when the needles were removed filling the pores and occluding the perforations as shown in FIGS. 8A and 8B. This example demonstrates the importance of inserting needles through the mesh pores during the coating process in order to produce a perforated collagen coated P4HB mesh.

Figure 9A:
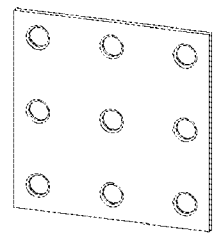
FIGS. 9A-D show four examples of different perforation patterns that can be introduced into a collagen coated mesh showing a square pattern (FIG. 9a), a diamond pattern (FIG. 9b), a circular pattern (FIG. 9c), and a random pattern (FIG. 9d).
Figure 9B:
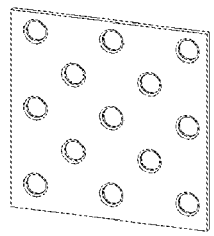
Figure 9C:
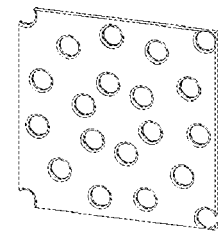
Figure 9D:
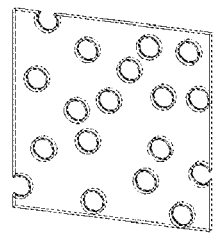
Figure 10A:
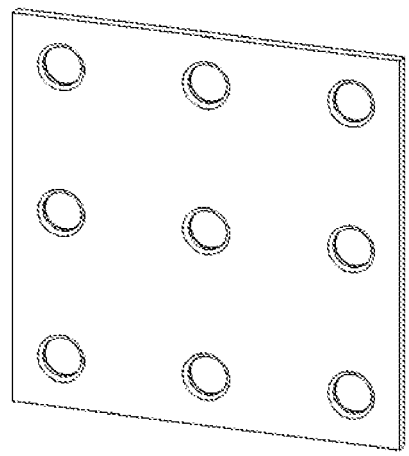
FIGS. 10A and 10B show two examples of different perforation profiles that can be introduced into a collagen coated mesh showing a circular shape (FIG. 10a) and a diamond shape (FIG. 10b).
Figure 10B:
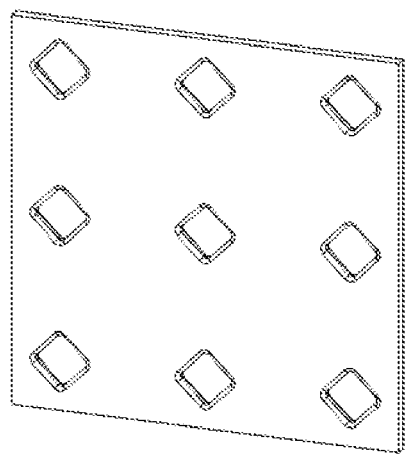

Example 6: Perforated Collagen Coated Meshes with Alternative Perforation Patterns and Profiles Perforated collagen coated meshes with alternative perforation patterns and profiles may be produced using the method described in examples 3 and 4. This may be accomplished by changing the configuration of the needles on the needle plate or the profile of the needles inserted into the needle plate. FIGS. 9A-9D show examples of four different perforation patterns that can be introduced into the collagen coated mesh. These are: (i) a square pattern (FIG. 9*a*), (ii) a diamond pattern (FIG. 9*b*) as described in Example 4, (iii) a circular pattern (FIG. 9*c*), and (iv) a random pattern (FIG. 9*d*). These perforation patterns can be produced by preparing different needle plates, for example, by press fitting needles in these patterns into a back plate (as described in Example 3) to form a new needle plate. FIGS. 10A and 10B shows two examples of different perforation profiles that can be introduced into the collagen coated mesh. These are (i) a circular shape (FIG. 10*a*) and a diamond shape (FIG. 10*b*). These perforation profiles can be produced by preparing different needle plates, for example, by press fitting needles with round or diamond cross-sections into a back plate (as described in Example 3) to form new needle plates. Once the new needle plates have been produced, the perforated collagen coated meshes, with different perforation patterns and profiles, can be produced by following the procedure described in Example 4.

Example 7: Preparation of a Cross-Linked Polypropylene (PP) Perforated Collagen Coated Mesh The mold shown in FIG. 1A was used to prepare a perforated polypropylene (PP) collagen coated mesh as follows. A polypropylene monofilament mesh made with 0.2 mm diameter monofilament fiber (BARD Mesh, CR Bard, Marlex knit) was cut to the size of the spacer rim plate (3) shown in FIG. 1A. The frame plates (4*a*, 4*b*, 4*c* and 4*d*) were then attached to the base plate (2) using the screws (6*a*; 6*b*; 6*c*; 6*d*; 6*e*; 6*f*; 6*g*; and 6*h*), and the needle plate (50) inserted into and through the base plate (2). The spacer rim plate (3) was then placed inside the mold on top of the base plate (2), and a solution of collagen (1% acid swollen bovine collagen gel, Collagen Solutions US Inc.) poured over the bed of the needle plate. The collagen solution was uniformly spread over the surface of the base plate (2) using a medical grade flexible brush. The polypropylene mesh was then loaded onto the needles and the mesh gently tapped down the needles until it was in full contact with the collagen solution spread on the base plate surface. This action forced the knit polypropylene fibers to adjust their positions around the perimeters of the needles, setting up the perforation pattern for the coated mesh. Additional collagen solution was poured over the mesh, and spread across the needles until all areas of the mesh were completely covered as shown in FIG. 1D where the mesh (10) is sandwiched between a bottom layer of collagen (11) and a top layer of collagen (12). The separation plate was then slid down the needles of the needle plate (50) until it made contact with the spacer rim plate (3), and the separation plate gently tapped to remove any excess collagen solution via the flow channels of the separation plate. The mold containing the collagen coated mesh was then placed in a freeze dryer with the bottom of the needle plate (50) in contact with the freezing shelf of the freeze dryer, and the unit frozen to −40° C. at a freezing rate between 5 and 15° C. per hour. After freezing, the frozen assembly was removed from the freeze dryer and inverted so that the bottom of the needle plate (50) was facing upward. A heating plate (FIG. 5A; 500) was fastened to the needle bed using mounting screws, slid into the holding frame (51) (FIG. 5B), and the heater turned on for 3-5 minutes to allow the needles to warm up and thaw the frozen composite in the vicinity of the needle stems. The needle plate (502) was then removed by lifting the heating plate (500) that was fastened to the needle bed, and the mold containing the frozen collagen coated mesh removed from the holding frame. The mold was disassembled by removing the frame plates (4), the spacer rim plate (3), and the separation plate (5), and the frozen collagen with entrapped mesh retrieved. While the collagen coated mesh was still frozen, it was placed on a stainless steel tray; a stainless steel mesh was placed over the frozen coated mesh to keep it flat, the tray put into a freeze-dryer, and the coated mesh dried over 15 hours to yield a dry perforated collagen coated polypropylene mesh.

The dried perforated collagen coated polypropylene mesh was placed in a vacuum chamber, and exposed to formaldehyde vapor for 1 hour to cross-link the collagen. After exposure of the collagen coated mesh to formaldehyde, the perforated cross-linked collagen mesh was aerated overnight.

The average burst strength and average suture pullout strength of the uncoated polypropylene mesh and the cross-linked perforated collagen coated mesh were determined by testing 5 samples of each, and the average results are shown in Table 3. As is evident from the results, the collagen coating perforation process did not negatively impact the mechanical properties of the underlying polypropylene mesh. Both the burst strength and suture pullout strength values for the uncoated polypropylene mesh and cross-linked perforated collagen coated polypropylene mesh were very similar.

TABLE 3

Mechanical Test Data for Cross-linked Perforated Collagen Coated Polypropylene (PP) Mesh

| Specimen Tested | Burst Strength (Avg. in kgf) | Suture Pull-out Strength (Machine Direction) (Avg. in kgf) |
|---|---|---|
| Cross-linked collagen coated perforated PP mesh | 35.2 | 5.8 |
| Uncoated PP mesh | 34.1 | 7.1 |

Modifications and variations of the methods and compositions will be apparent from the foregoing detailed description and are intended to come within the scope of the appended claims.

We claim:

1. An implant comprising: a monofilament knitted mesh coated with collagen,
   wherein the mesh comprises pores,
   wherein the mesh further comprises perforations forming channels through the implant,
   wherein the perforations are enlarged pores, and
   wherein the enlarged pores have an average diameter greater than an average diameter of the pores in the mesh.

2. The implant of claim 1 wherein the mesh coated with collagen has at least 65% of the burst strength of the mesh measured when the mesh is not coated with collagen.

3. The implant of claim 1 wherein the collagen is cross-linked.

4. The implant of claim 1 wherein the mesh is a poly-4-hydroxybutyrate mesh, polypropylene mesh or polyester mesh.

5. The implant of claim 1 wherein the mesh comprises poly-4-hydroxybutyrate or a copolymer thereof.

6. The implant of claim 1, wherein the implant is three dimensional in shape, and wherein the length of the channels span a thickness of the implant.

7. The implant of claim 6, wherein the mesh is resorbable.

8. The implant of claim 6, wherein the mesh comprises poly-4-hydroxybutyrate.

9. The implant of claim 1 wherein the perforations in the implant are located in a random, ordered, or patterned manner.

10. The implant of claim 1 wherein the shape of the perforations in the implant are circles, ellipses, triangles, squares, and polygons.

11. The implant of claim 1 wherein the monofilament knitted mesh coated with collagen has one or more of the following properties that are within 20% of a value of the monofilament knitted mesh prior to coating with collagen: (i) burst strength, (ii) suture pullout strength, and (iii) tensile strength.

12. A method of forming the implant of claim 1, the method comprising the steps of:
    positioning needles through pores of a monofilament knitted mesh,
    coating the monofilament knitted surgical mesh with a collagen solution thereby forming the perforated collagen coated mesh,
    freezing the perforated collagen coated mesh,
    removing the needles from the pores of the frozen perforated collagen coated mesh, and
    drying the perforated collagen coated mesh.

13. The method of claim 12 wherein the monofilament knitted mesh with needles through pores of the monofilament knitted mesh is brought into contact with the collagen solution on a first side of the monofilament knitted surgical mesh to encase the first side of the monofilament knitted mesh with collagen, and additional collagen solution is added to a second side of the monofilament knitted mesh to encase the monofilament knitted mesh with the collagen.

14. The method of claim 12 further comprising heating the needles before removing the needles from the pores of the perforated collagen coated mesh.

15. The method of claim 12 wherein the perforated collagen coated mesh is dried by freeze-drying.

16. The method of claim 12 further comprising heat setting the monofilament knitted mesh after positioning the needles through the pores of the monofilament knitted mesh.

17. The method of claim 16 comprising:
    removing the heat set monofilament knitted mesh from the needles,
    pouring the collagen solution on the needles and relocating the monofilament knitted mesh in the same position on the needles prior to removing the heat set monofilament knitted mesh from the needles.

18. The method of claim 12 further comprising cross-linking the collagen.

19. The method of claim 12 wherein the implant has one or more of the following properties: average thickness between 0.1 mm and 25 mm, perforations with diameters from 0.1 mm to 10 mm, density of perforations from 1 to 50 per square cm, and burst strength between 1 kgf and 100 kgf.

20. The method of claim 12 wherein the needles are tapered.

21. The method of claim 12 wherein the implant is formed using an assembly comprising:
    a needle plate comprising the needles in a pattern, fit onto a back plate,
    a base plate comprising holes matching the needle pattern on the needle plate,
    frame plates that attach to the base plate to form a container for the collagen solution,
    a spacer rim plate, and
    a perforated separation plate with holes matching the needle pattern on the needle base plate.

22. The method of claim 21 comprising forming an assembly by:
    (i) positioning the needles of the needle plate through the pores of the monofilament knitted mesh, and heat setting the monofilament knitted mesh on the needle plate,
    (ii) removing the monofilament knitted mesh is removed from the needle plate, and inserting the needle plate into the base plate until the needle plate is flush against one side of the base plate with the needles protruding from the other side of the base plate,
    (iii) attaching the frame plates each side of the base plate to form a container,
    (iv) placing the spacer rim plate on top of the base plate and inside the container formed by the frame plates,
    (v) pouring the collagen solution to cover the base plate to a desired depth,
    (vi) placing the heat set monofilament knitted mesh on the needles in a same orientation as used for heat setting until the monofilament knitted mesh is in contact with the collagen solution,
    (vii) pouring the collagen solution on top of the monofilament knitted mesh to cover the monofilament knitted mesh, (viii) sliding the perforated separation plate down the needles of the needle plate until the perforated separation plate contacts the spacer rim plate, (ix) freezing the assembly to form the perforated collagen coated mesh, (x) heating the needles of the needle plate, wherein the assembly is subsequently disassembled to release the perforated frozen collagen coated mesh, and (xi) freeze drying the perforated collagen coated mesh.

23. The method of claim 22 further comprising cross-linking the perforated collagen coated mesh with formaldehyde.

24. The method of claim 22 further comprising one or more of the following steps: adding graduated markings to the perforated collagen coated mesh, cutting the perforated collagen coated mesh; packaging the perforated collagen coated mesh and sterilizing the perforated collagen coated mesh.

25. The method of claim 24 wherein the perforated collagen coated mesh is sterilized with ethylene oxide.

26. The method of claim 22 further comprising keeping the perforated collagen mesh flat while it is freeze-dried.

27. The method of claim 22 wherein the perforated collagen coated mesh is frozen to a temperature of −40° C.±10° C., and freeze-dried using a lyophilizer over a period of 5 to 20 hours.

28. The method of claim 12 wherein the monofilament knitted mesh is resorbable or permanent.

29. The method of claim 12 wherein the monofilament knitted mesh is made from a polymer comprising one or more of the following monomers: glycolic acid, lactic acid, trimethylene carbonate, p-dioxanone, ε-caprolactone, 3-hydroxybutyrate, and 4-hydroxybutyrate.

30. The method of claim 12 wherein the monofilament knitted mesh is made from one of the following polymers or a blend of the following polymers: poly(lactide); poly(glycolide); poly(lactide-co-glycolide); poly(lactic acid); poly(glycolic acid); poly(lactic acid-co-glycolic acid); polycaprolactone; poly(orthoester); polyanhydride; poly(phosphazene); polyhydroxyalkanoate; poly-3-hydroxybutyrate, poly-4-hydroxybutyrate-co-3-hydroxyvalerate, poly-4-hydroxybutyrate; poly-3-hydroxybutyrate-co-4-hydroxybutyrate; synthetically or biologically prepared polyester; polycarbonate; tyrosine polycarbonate; polyamide; polyesteramide; poly(dioxanone); poly(alkylene alkylate); polyether, polyethylene glycol, polyethylene oxide, polyvinyl pyrrolidone; polyurethane; polyetherester; polyacetal; polycyanoacrylate; poly(oxyethylene)/poly(oxypropylene) copolymer; polyacetal, polyketal; polyphosphate; phosphorous-containing polymer; polyphosphoester; polyalkylene oxalates; polyalkylene succinates; poly(maleic acid); chitin; chitosan; modified chitosan; biocompatible polysaccharide; biocompatible copolymers, block copolymers and random copolymers; hydrophilic or water soluble polymer; polymers and copolymers of ethylene and propylene, polypropylene, polyethylene, ultra-high molecular weight polyethylene, ultra-high molecular weight polypropylene, nylon, polyester, poly(ethylene terephthalate), poly(tetrafluoroethylene), polyurethane, poly(ether-urethanes), poly(methylmethacrylate), polyether ether ketone, and polyolefin.

31. The method of claim 12 wherein the implant is: (a) dimensioned for use as an implant or (b) trimmable to a predetermined shape.

32. The method of claim 12 wherein the monofilament mesh is made from poly-4-hydroxybutyrate.

33. The method of claim 12 wherein the perforated collagen coated mesh has one or more of the following properties that are within 20% of a value of the monofilament knitted mesh prior to coating with collagen: (i) burst strength, (ii) suture pullout strength, and (iii) tensile strength.

34. A method of using the implant of claim 1 comprising: implanting the implant in a body or applying the implant topically to a surface of the body.

35. The method of claim 34 wherein the implant is used for soft or hard tissue repair.

36. The method of claim 35 wherein the implant is used in plastic surgery, mastopexy, breast reconstruction, hernia repair, treatment of urinary incontinence, pelvic floor reconstruction, ligament and tendon repair, or lift procedures including face lift, neck lift, eyebrow lift and breast lift.

37. An implant comprising: a mesh coated with collagen,
wherein the mesh comprises pores,
wherein the mesh further comprises perforations forming channels through the implant,
wherein the perforations are enlarged pores,
wherein the enlarged pores have an average diameter greater than an average diameter of the pores, and
wherein the mesh is made from monofilament fibers with average diameters between 0.001 mm and 1.0 mm.

38. The implant of claim 37 wherein the collagen is cross-linked.

39. The implant of claim 37 wherein the mesh is a poly-4-hydroxybutyrate mesh, polypropylene mesh or polyester mesh.

40. The implant of claim 37, wherein the mesh is a poly-4-hydroxybutyrate mesh.

41. An implant comprising: a mesh embedded between two collagen layers,
wherein the mesh comprises pores,
wherein the mesh further comprises perforations,
wherein the perforations are enlarged pores,
wherein the enlarged pores have an average diameter greater than an average diameter of the pores,
wherein the mesh is a poly-4-hydroxybutyrate mesh, polypropylene mesh or polyester mesh,
wherein the implant is three dimensional in shape, and the perforations span a thickness of the implant.

42. The implant of claim 41 wherein the mesh is a poly-4-hydroxybutyrate mesh.

43. The implant of claim 41, wherein the mesh is a monofilament knitted mesh.

* * * * *

UNITED STATES PATENT AND TRADEMARK OFFICE
CERTIFICATE OF CORRECTION

PATENT NO. : 10,532,127 B2  
APPLICATION NO. : 15/354664  
DATED : January 14, 2020  
INVENTOR(S) : Skander Limem, Bhavin Shah and Said Rizk It is certified that error appears in the above-identified patent and that said Letters Patent is hereby corrected as shown below:

In the Specification

Column 2, Line 18, replace "method to produced perforated" with --method to produce perforated--.
Column 3, Line 52, replace "602h and 602d" with --602h and 602i--.
Column 7, Lines 27-29, replace "(obtained is a collagen coat is merely applied onto a polymeric mesh for example" with --(obtained when a collagen coat is merely applied onto a polymeric mesh for example)--.
Column 9, Line 3, replace "tetrahydofurfuryl" with --tetrahydrofurfuryl--.
Column 9, Line 37, replace "types I to XIII" with --types I to XIII.--.
Column 12, Lines 42-43, replace "By contrast, the methods disclosed herein by contrast provide" with --By contrast, the methods disclosed herein provide--.
Column 13, Line 12, replace "kfg" with --kgf--.
Column 15, Line 65, replace "holes (6a; 6b; 6c; 6d; 6e; 6f; 6g and 6h)" with --holes (104a, 104b, etc.)--.
Column 16, Line 2, replace "(504a-505c in FIG. 5A)" with --(504a-504c in FIG. 5A)--.
Column 17, Line 66, replace "(8A, 8b; etc.)" with --(8a, 8b; etc.)--.
Column 22, Lines 60-61, replace "(508a; 508; 508c; etc.)" with --(508a; 508b; 508c; etc.)--.

In the Claims

Claim 22, Column 28, Lines 50-51, replace "removing the monofilament knitted mesh is removed from the needle plate" with --removing the monofilament knitted mesh from the needle plate--.

Signed and Sealed this
Twenty-eighth Day of July, 2020

Andrei Iancu
*Director of the United States Patent and Trademark Office*